(12) United States Patent
Degertekin et al.

(10) Patent No.: US 7,107,825 B2
(45) Date of Patent: Sep. 19, 2006

(54) METHOD AND APPARATUS FOR THE ACTUATION OF THE CANTILEVER OF A PROBE-BASED INSTRUMENT

(75) Inventors: F. Levent Degertekin, Decatur, GA (US); Chanmin Su, Ventura, CA (US); Peter G. Neilson, Santa Barbara, CA (US)

(73) Assignee: Georgia Tech Research Corporation, Atlanta, GA (US)

(*) Notice: Subject to any disclaimer, the term of this patent is extended or adjusted under 35 U.S.C. 154(b) by 83 days.

(21) Appl. No.: 10/456,136

(22) Filed: Jun. 6, 2003

(65) Prior Publication Data
US 2004/0020279 A1 Feb. 5, 2004

Related U.S. Application Data

(63) Continuation-in-part of application No. 10/095,850, filed on Mar. 12, 2002, now Pat. No. 6,779,387.

(60) Provisional application No. 60/313,911, filed on Aug. 21, 2001.

(51) Int. Cl.
G01B 5/28 (2006.01)
(52) U.S. Cl. .................................................. 73/105
(58) Field of Classification Search ................ 73/105, 73/81, 82; 324/762, 765–769; 250/306, 250/307
See application file for complete search history.

(56) References Cited

U.S. PATENT DOCUMENTS 4,079,460 A * 3/1978 de Leeuw ..................... 365/25
6,006,593 A * 12/1999 Yamanaka ................... 73/105

\* cited by examiner

*Primary Examiner*—Robert Raevis
(74) *Attorney, Agent, or Firm*—Boyle Fredrickson Newholm Stein & Gratz S.C.

(57) ABSTRACT

An electromagnetic drive causes a cantilever of a probe-based instrument to deform flexurally by transmitting a high frequency AC signal through an electromagnetic actuator located in the vicinity of the cantilever. The AC signal preferably is an RF carrier signal having a frequency that is substantially higher than the resonant frequency of the cantilever. The carrier signal may, if desired, be modulated with a lower frequency modulation signal to induce the cantilever to oscillate, preferably at resonance. Alternatively, the carrier signal may be transmitted to the electromagnetic actuator without being modulated in order to deflect the cantilever quasi-statically. Cantilever response can then be monitored either directly in response to the imposition of the electromagnetically induced deformation of the cantilever in response to probe/sample interaction to obtain measurements regarding characteristics of the sample, the environment, and/or the cantilever.

41 Claims, 23 Drawing Sheets

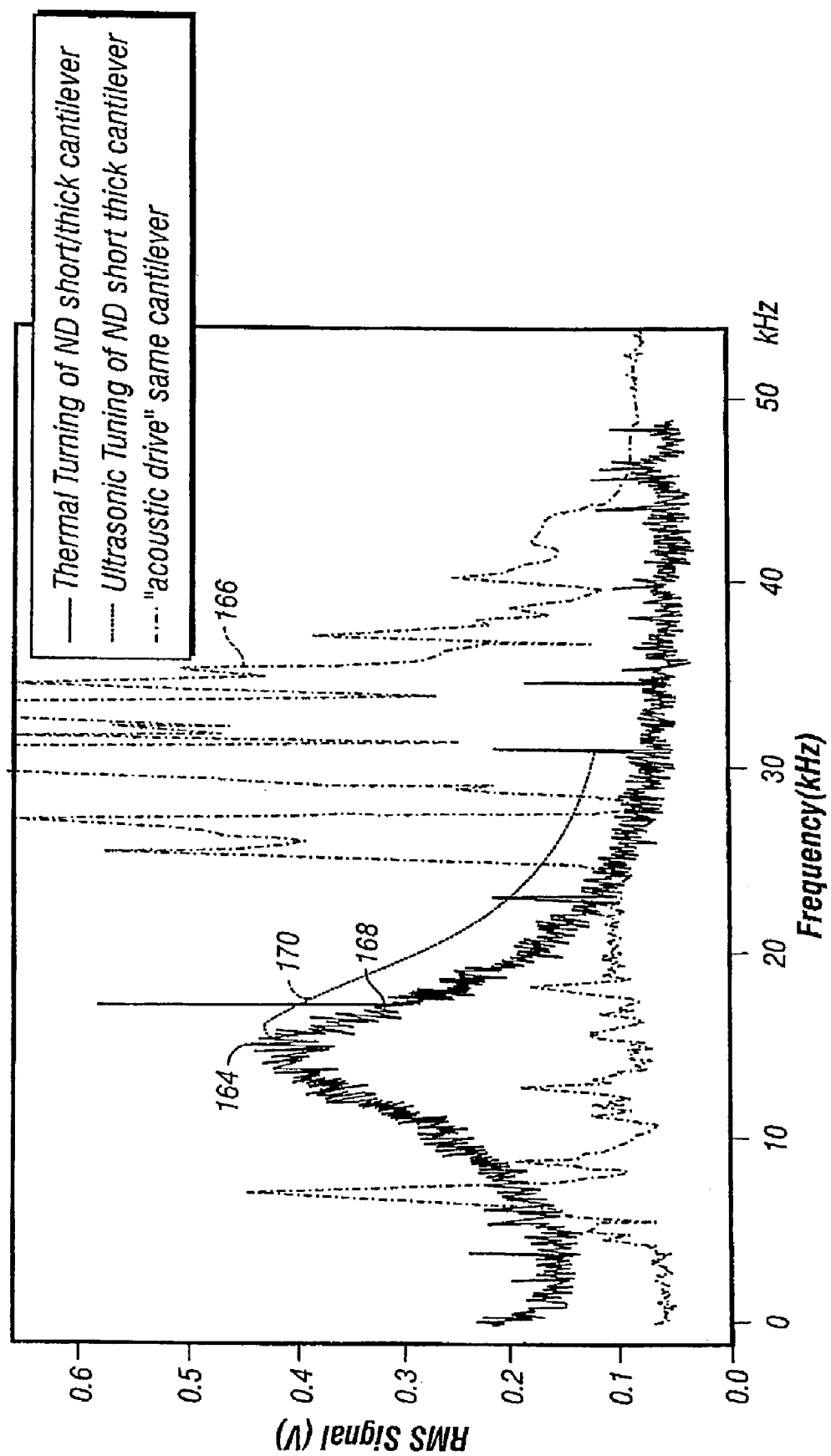

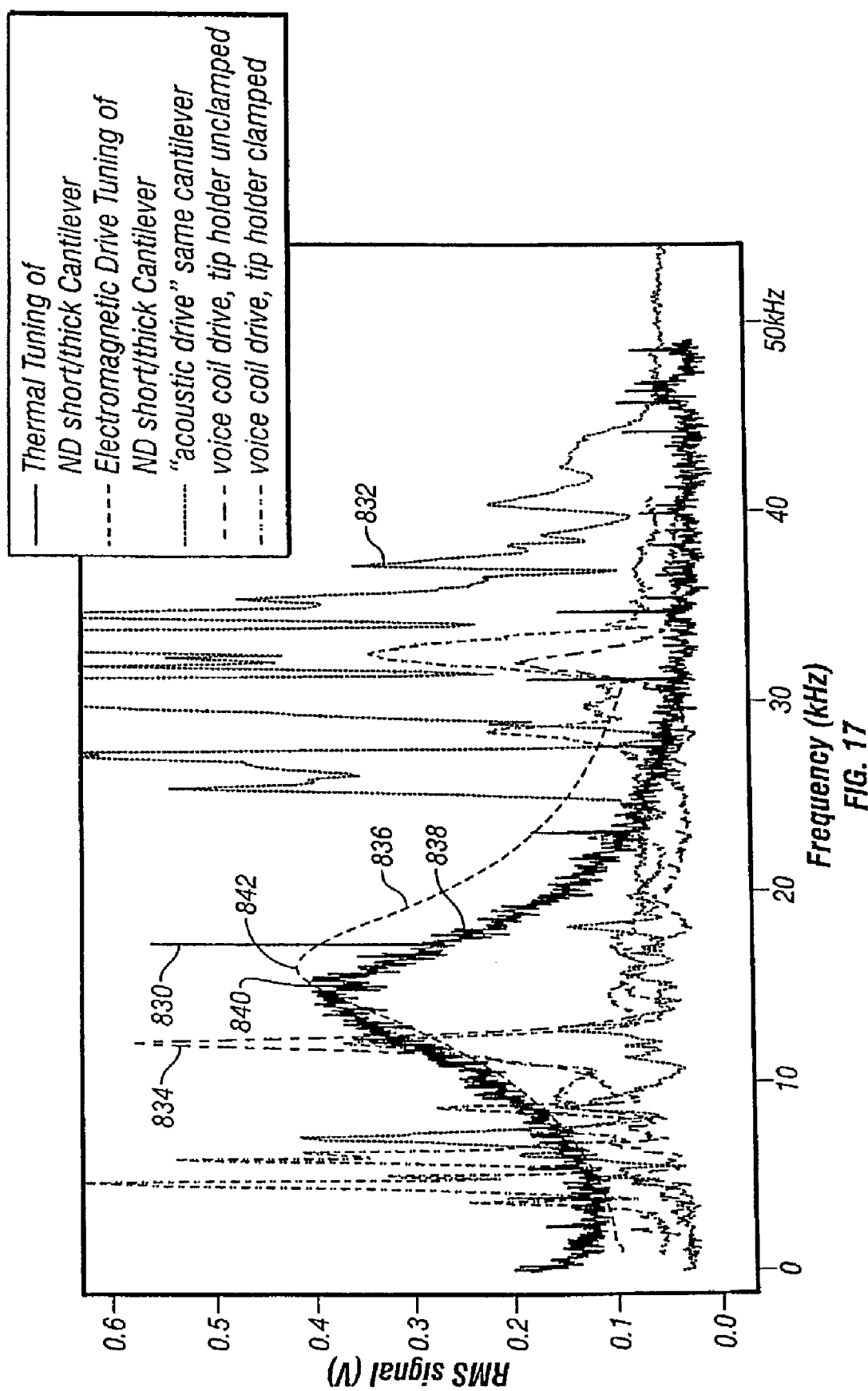

METHOD AND APPARATUS FOR THE ACTUATION OF THE CANTILEVER OF A PROBE-BASED INSTRUMENT

CROSS-REFERENCE TO RELATED APPLICATION

This is a continuation-in-part of U.S. patent application Ser. No. 10/095,850, entitled "Method and Apparatus for the Ultrasonic Actuation of the Cantilever of a Probe-Based Instrument," filed Mar. 12, 2002 now U.S. Pat. No. 6,779,387 which, in turn, claims priority under 35 USC §1.119(e) on prior U.S. Provisional Patent Application Ser. No. 60/313,911, filed Aug. 21, 2001. The subject matter of both applications is hereby incorporated by reference in their entirety.

BACKGROUND OF THE INVENTION

1. Field of the Invention

The present invention is directed to probe-based instruments and, more particularly, relates to a method and apparatus for driving a cantilever of such an instrument using either acoustic radiation pressure generated by an ultrasonic actuator or an interaction generated by an electromagnetic drive.

2. Description of Related Art

Several probe-based instruments monitor the interaction between a cantilever-based probe and a sample to obtain information concerning one or more characteristics of the sample. For example, scanning probe microscopes (SPMs) typically characterize the surface of a sample down to atomic dimensions by monitoring the interaction between the sample and a tip on the cantilever probe. By providing relative scanning movement between the tip and the sample, surface characteristic data can be acquired over a particular region of the sample, and a corresponding map of the sample can be generated.

The atomic force microscope (AFM) is a very popular type of SPM. The probe of the typical AFM includes a very small cantilever which is fixed to a support at its base and which has a sharp probe tip attached to the opposite, free end. The probe tip is brought very near to or into contact with a surface of a sample to be examined, and the deflection of the cantilever in response to the probe tip's interaction with the sample is measured with an extremely sensitive deflection detector, often an optical lever system such as described in Hansma et al. U.S. Pat. No. RE 34,489, or some other deflection detector such as strain gauges, capacitance sensors, etc. The probe is scanned over a surface using a high-resolution three axis scanner acting on the sample support and/or the probe. The instrument is thus capable of creating relative motion between the probe and the sample while measuring the topography or some other surface property of the sample as described, e.g., in Hansma et al. U.S. Pat. No. RE 34,489; Elings et al. U.S. Pat. No. 5,226,801; and Elings et al. U.S. Pat. No. 5,412,980.

AFMs may be designed to operate in a variety of modes, including contact mode and oscillating mode. In contact mode operation, the microscope typically scans the tip across the surface of the sample while keeping the force of the tip on the surface of the sample generally constant. This effect is accomplished by moving either the sample or the probe assembly vertically to the surface of the sample in response to sensed deflection of the cantilever as the probe is scanned horizontally across the surface. In this way, the data associated with this vertical motion can be stored and then used to construct an image of the sample surface corresponding to the sample characteristic being measured, e.g., surface topography. Alternatively, some AFMs can at least selectively operate in an oscillation mode of operation such as TappingMode™. In TappingMode™ the tip is oscillated at or near a resonant frequency of the cantilever of the probe. The amplitude or phase of this oscillation is kept constant during scanning using feedback signals, which are generated in response to tip-sample interaction. As in contact mode, these feedback signals are then collected, stored, and used as data to characterize the sample.

Regardless of their mode of operation, AFMs can obtain resolution down to the atomic level on a wide variety of insulating or conductive surfaces in air, liquid or vacuum by using piezoelectric scanners, optical lever deflection detectors, and very small cantilevers fabricated using photolithographic techniques. Because of their resolution and versatility, AFMs are important measurement devices in many diverse fields ranging from semiconductor manufacturing to biological research.

One potentially problematic characteristic of AFMs and other probe-based instruments lies in the technique employed to provide an external force to deflect or oscillate the instrument's cantilever. In an AFM, the cantilever is typically oscillated using a piezoelectric drive, often known simply as a piezo drive. Referring to FIG. 1A by way of example in this type of system, the typical probe 20 includes a cantilever 22 that extends outwardly from a substrate 26 coupled to a piezoelectric drive 24 via a probe mount 27. Probe 20 also includes a tip 28 that is provided on the opposed, free end of the cantilever 20. The piezoelectric drive 24 can be selectively excited by a signal generator 29 to move the cantilever 22 up and down relative to a sample 30. When the instrument is configured for an oscillating mode of operation, the drive voltage is applied to the piezoelectric drive 24 to drive the cantilever 22 to oscillate at a frequency that is dependent upon the frequency of the drive voltage. This frequency is typically at or near the cantilever's resonant frequency, particularly when the instrument is operated in TappingMode™.

Such a traditional piezoelectric drive necessarily acts only on the base of the cantilever, not on the free end portion. It therefore must apply substantially greater forces to the cantilever to obtain a given deflection magnitude at the free end than it would if it were to apply forces directly to the free end or even to the body of the cantilever. This inefficiency limits the range of applications for this common type of piezo-electrically-driven probe.

For instance, the piezoelectric drive shown in FIG. 1A works well in air because the typical AFM cantilever can be excited to resonance in air relatively easily. This characteristic is quantified by the "quality factor" of a resonance of the cantilever. The quality factor, Q, denotes the sharpness of a cantilever's resonance curve as denoted by the ratio: $f_0/\Delta f$ where $f_0$ is the resonant frequency and $\Delta f$ is the bandwidth between the half-power points of the curve as reflected by the half-peak amplitude points 41a and 41b on the curve 40 in FIG. 2A. The curve 40 demonstrates that the typical cantilever operating in air has a Q of 100–200 or even higher. The Q of a cantilever resonance is a measure of how much gain the resonance provides in an oscillating system. A resonance with a large Q can be excited to relatively large cantilever oscillation amplitudes with relatively small excitation forces. For operation in air or other gaseous environments, the cantilever typical piezoelectric drive usually has ample excitation force to drive the cantilever to produce a resonance peak 42 that is easily identified and distinguished from other, parasitic resonance peaks such as those of the mounts for the cantilever and the piezoelectric drive and the piezo material itself (note the much smaller peaks 42a, 42b, etc. denoting these parasitic resonances).

Conversely, a cantilever operated in liquid such as water has a dramatically lower Q because the liquid damps the oscillating cantilever. In fact, the typical cantilever operating in water can have a Q of less than 30 and even less than 10. As a result, the typical piezoelectric drive does not have enough gain to excite the cantilever sufficiently to produce a resonance peak that is easily located and differentiated from parasitic resonances. This effect is discussed below in conjunction with FIG. 2B.

Specialized cantilever drives are available that act along the length of the cantilever rather than only on the base. One such drive is the so-called magnetic drive. Referring to FIG. 1B, the typical magnetic drive system 50 has a magnetic cantilever 52 that is driven by an electromagnetic drive. The cantilever 52 has a fixed base rigidly attached to a support 54 and bears a tip 56 on its free end that interacts with sample S. The cantilever is also rendered magnetic by coating one or more of its surfaces with a magnetic layer 58. The static electromagnetic drive comprises at least one electromagnet coil 60 spaced from the cantilever 52. The coil(s) can be energized by a controller 62 including a signal generator to impose a variable magnetic field on the magnetic layer 58. The magnetic field produces a torque on the cantilever 52 of a magnitude that increases with the amplitude of the applied magnetic field acting on the layer 58. By controlling the amplitude of the applied magnetic field, the cantilever 52 can be deflected as desired while the tip 56 interacts with the sample S. This deflection is monitored by a photodetector 66 receiving reflected light transmitted by a laser 68. In the usual case in which the magnetic drive 60 is controlled to maintain a specified characteristic of cantilever deflection constant during scanning, an output signal related to the amplitude of the signal provides an indication of a surface force applied to the probe. A magnetic drive system having these characteristics is described in greater detail in U.S. Pat. No. 5,670,712 to Cleveland, the subject matter of which is hereby incorporated by reference by way of background.

A magnetic drive system has inherent limitations that considerably restrict its range of applications. For instance, it requires a special magnetically coated cantilever and, accordingly, cannot be used in applications in which the cantilever is not capable of being coated with a magnetic material. It also is not usable in applications in which magnetic properties of the sample and/or the environment cause unwanted deflection of the cantilever and introduce errors into the measurements. The practical operating ranges of the magnetic drive system are also limited. A typical magnetic drive coil may operate with a current exceeding one amp and result in a cantilever deflection on the order of 1–100 nm at the cantilever resonance frequency generated can cause thermal drift errors in the measurement of the AFM. The frequency range of the magnetic drive system is also limited by the inductance of the drive coil. Higher actuation forces can be achieved by using more loops in the drive coil, but this also increases the inductance and limits the maximum operating frequency. With the limits of inductance and maximum heat load, the typical magnetic drive operates at less than 50 kHz and with oscillation amplitudes of less than 30 nm. For example, the MAC-Mode™ magnetic drive system, sold by Molecular Imaging, advertises an operating range of 5–30 kHz and a maximum amplitude of 30 nm.

Another instrument having a cantilever driven other than from its base utilizes the so-called acoustic drive. Referring to FIG. 1C, in an instrument 70 of this type, a cantilever 71 and a piezoelectric drive 72 are mounted on a common head 74 in a spaced-apart relationship. The head 74 is mounted above a fluid cell 76 by mounting balls 78 or other supports so that the cantilever 71 extends into the fluid cell 76 so as to interact with a sample (not shown) in the cell. The piezoelectric drive 72 can be excited by a signal generator 80 to generate acoustic waves that propagate through the glass walls of the fluid cell 76, through the fluid in the cell 76, and onto the cantilever 71, causing the cantilever 71 to oscillate. An acoustic drive having these characteristics is disclosed, for example, in Putman et al in "Tapping Mode Atomic Force Microscopy in Liquids" Applied Physics Letters 64: 2454–2456.

Acoustic drive has distinct disadvantages that limit its effectiveness. For instance, the acoustic energy also impinges on many other components of the system, such as mounts for the cantilever and the piezoelectric drive, the fluid cell, and even the fluid, exciting resonances in those components. These resonances can be difficult to distinguish from the cantilever resonance. The acoustic drive also has sufficient actuation force at a limited selection of operation frequencies and it can be a challenge to match the cantilever resonance with the operation frequency of the acoustic actuator. If a user selects a resonance that does not overlap with the cantilever resonance, the measurements may be unstable.

An ultrasonic force microscope (UFM) is a scanning probe microscope that uses high frequency acoustic waves to image the mechanical properties of a sample, often showing sub-surface contrast. Specifically, referring to FIG. 1D, a UFM 90 includes a cantilever 91 having a base fixed to a stationary support 94, a sample support 92 located beneath the cantilever 91, and on an XYZ scanner 96 that supports the sample support. An ultrasonic actuator 98 such as a commercial ultrasound transducer mounted on the bottom of the sample support 92 is excited by an RF voltage from an RF signal generator 100. The ultrasonic actuator 98 is relatively large (typically a centimeter or more in diameter) with a resonant frequency often in the low-MHz range. When it is excited by the RF signal generator 100, it generates ultrasonic waves that impinge over a broad area of the sample S. Some of the incident ultrasonic energy is reflected or absorbed, and some penetrates the sample S and then impinges on the cantilever 91, causing the cantilever 91 to deflect away from the sample surface. The magnitude of the cantilever deflection is related to the percentage of the energy that penetrates the sample S and, accordingly, reflects variation in sample properties such as density. Accordingly, as the sample S is scanned relative to the probe using the scanner 96, variations in cantilever deflection can be detected to provide information concerning the sample. In addition, while UFMs have been in use for almost a decade, no one has adapted an ultrasonic device as a general purpose cantilever actuator capable of deflecting the cantilever at a wide range of frequencies. In the UFMs, the tip must be in contact with the sample surfaces. The ultrasonic energy is transferred into cantilever deflection through surface displacement of the sample. Such an energy transfer mechanism requires constant contact of the tip with sample surfaces, and would not work in the case of TappingMode AFM where the tip is in contact with surfaces only 1 to a few percent of time.

Turning to FIG. 2B mentioned above, the plots demonstrate the frequency response of a typical AFM cantilever to excitation. The curve 44 plots the actual or true response of a relatively short and thick cantilever in water as determined by a known process called a "thermal tune." A thermal tune measures the natural intrinsic motion of the cantilever in response to the temperature driven molecular motion of its surroundings. Basically, the "heat bath" that surrounds the cantilever provides the energy to naturally oscillate the cantilever at a very small amplitude, usually sub-nm. Since the cantilever oscillation amplitude due to the thermal energy is so small, thermal tunes cannot be used for image data acquisition, but they do provide a very clean representation of the true oscillatory response of the cantilever. The curve 46 plots the detected response of the same cantilever as it is driven acoustically by a piezoelectric drive (FIG. 1C). The true response as denoted in curve 44 has a sharp peak 48 at the fundamental resonance of about 15 kHz. However, when the cantilever is driven acoustically by a piezoelectric drive, fluid damping and other effects reduce that response to the point that the cantilever resonance peak cannot be differentiated from parasitic resonance peaks. The parasitic resonances often dominate the response spectra.

Hence, the need has arisen to provide a probe-based instrument that has an actuator that drives the cantilever 50 as to produce a "clean" frequency response, preferably by driving the cantilever body rather than the base, but that is versatile in bandwidth/or types of measurements.

The need has also arisen to provide an improved method of driving a cantilever of a probe-based instrument.

SUMMARY OF THE INVENTION

In accordance with a first aspect of the invention, one or more the above-identified needs is met by providing a probe-based instrument having a cantilever that is deflected by directing acoustic waves onto the body of the cantilever rather than by moving the base of the cantilever. The cantilever is deflected by a second order force, also known as an acoustic radiation pressure, generated by beams of ultrasonic energy produced by an ultrasonic actuator such as a zinc oxide transducer. The ultrasonic actuator is supplied with an oscillating RF voltage that may be continuous or varied in a quasistatic manner to apply a constant or changing force to the cantilever. The RF voltage may also be modulated at any frequency from DC to many MHz, thus providing an ideal drive force for oscillating the cantilever over an extremely wide range of frequencies. Driving the body of the cantilever with an ultrasonic actuator produces a much higher localized force than can be achieved through the use of a traditional piezoelectric actuator and, accordingly, permits a "clean" frequency response where the resonance peak is easily identified and parasitic resonance peaks due to overdrive of the tip holder or other mechanical parts completely eliminated. This, in turn, dramatically improves the accuracy, precision, and stability of the measurement, and increases the system's bandwidth, particularly when the cantilever operates in a liquid. The method implemented by the invention can be used to actuate cantilevers with arbitrary shapes and materials, eliminating the requirement for magnetic or piezoelectric coatings on the cantilever. The method and system of the preferred embodiments also are useful in imaging in liquids and quantitative measurements of surfaces and molecular-scale samples in liquids. The method and system of the preferred embodiments also are useful in AFM measurements in other fluids including air.

The improved frequency response of the ultrasonic actuator of one preferred embodiment also yields a dramatically higher bandwidth than traditional piezoelectric actuators, rendering them useful in a variety of applications and with a variety of cantilevers beyond those available with conventional piezoelectric actuators.

The beam is preferably "shaped", i.e., manipulated to limit unwanted propagation in directions other than toward the cantilever, so that ultrasonic energy impinges at least primarily on the cantilever. Two suitable techniques for shaping the beam are focusing and collimation. Ultrasonic beams can be focused on the cantilever using a Fresnel lens or another focusing device located between the ultrasonic actuator and the cantilever. Collimation requires only that the ultrasonic actuator be suitably sized, positioned, and driven to reduce beam divergence sufficiently to achieve the desired effect.

Cantilever deflection may be measured by a conventional photodetector, in which case the photodetector, a laser, and the ultrasonic actuator are all preferably positioned on a common side of the cantilever opposite the sample support. Cantilever deflection may also be detected using another device such as a simple interferometer located over the cantilever body.

In accordance with another aspect of the invention, one or more of the above-identified needs is met by providing a probe-based instrument having a cantilever driven by an "electromagnetic drive." The electromagnetic drive applies a force directly to the cantilever when a high frequency AC signal is transmitted to an "electromagnetic actuator" positioned in the vicinity of the cantilever. Energization of the electromagnetic actuator with the AC signal imposes a force on the cantilever that tends to bend the cantilever. The force is believed to be generated at least in part by an induced electromagnetic (IEM) interaction resulting from the energization of the electromagnetic actuator with the AC signal. It may also be generated at least in part by thermal stress gradient and/or electrostrictive stresses that are induced in the cantilever as a result of electromagnetic actuator energization. The AC signal is formed at least in part from a carrier signal having a frequency that is substantially higher than the resonant frequency of the cantilever, and will typically in the neighborhood of 10–300 MHz. If desired, the high frequency carrier signal can be modulated with a lower frequency modulation signal, typically on the order of a few hundred kHz, to induce the cantilever to oscillate, preferably at resonance. The cantilever can be rendered conductive, e.g., by coating all or part of at least one of its surfaces with a layer of conductive material or by forming the cantilever from doped silicon. The electromagnetic actuator may comprise, e.g., a micro wire or a conductive pattern fixed on a substrate located in the vicinity of the cantilever. The resulting drive has all the benefits of the ultrasonic actuator described above and has the additional benefit of being able to effectively operate in both gases and fluids, whereas an ultrasonic actuator only operates effectively in liquids.

These and other features and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

A preferred exemplary embodiment of the invention is illustrated in the accompanying drawings in which like reference numerals represent like parts throughout, and in which:

FIG. 7A is a family of curves illustrating the response of a cantilever of the system of FIG. 3B to an oscillating input drive signal in liquid using both a prior art actuator and the actuator of FIG. 3B;

FIGS. 17, 17A, and 18 are graphs comparing the response of various different cantilever drive systems and operating environments to changes in RF input frequency;

DETAILED DESCRIPTION OF THE PREFERRED EMBODIMENTS

As discussed briefly in the Summary section above, the invention lies in the provision of an ultrasonic drive or an electromagnetic drive for a probe based instrument. Both drives deflect a cantilever by imposing a force at or near the tip of the cantilever (and possibly along other portions of the cantilever as well) as opposed to only at its base. Both drives also are relatively immune to parasitic losses and exhibit very high frequency response bandwidths. As a practical matter, the drives vary from one another primarily in that an ultrasonic drive is effective only in liquids, whereas an electromagnetic drive is effective in either liquids or gases. Both drives, and possible applications and variations of them, will be discussed in turn.

I. Ultrasonic Drive

An ultrasonic drive relies on ultrasonically generated acoustic radiation pressure to deflect a cantilever of a probe-based instrument. It is particularly well suited, but in no way limited, for instruments configured to take measurements in a liquid such as water or other aqueous solutions. A variety of SPMs and other instruments may benefit from this technique. Hence, while several different AFMs incorporating the invention will now be described by way of example, it must be emphasized that the invention is not limited to the described embodiments or even to AFMs in general. To the contrary, it is applicable to virtually any cantilever-based instrument in which a cantilever is deflected by directing a beam of ultrasonic energy at the cantilever to apply ultrasonically generated acoustic radiation pressure to the cantilever. The beam preferably is shaped, either by focusing substantially onto a surface of the cantilever, or by generating a sufficiently collimated or minimally divergent beam to permit to at least a portion of the beam to strike the cantilever. A variety of different ultrasonic actuators and associated drives may be employed to achieve these effects, and cantilever deflection may be measured using a variety of techniques.

A. Theory of Operation

Figure 3A:
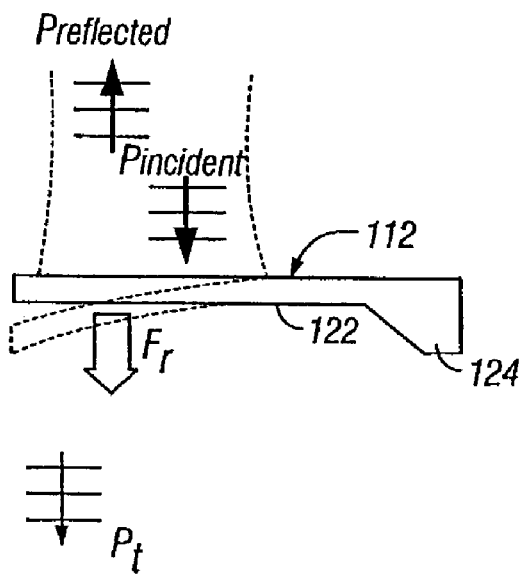
FIG. 3A schematically illustrates the deflection of a cantilever of an AFM using ARP.

A plane target placed in the path of an acoustic wave beam in an unconfined medium experiences a time averaged force per unit area. This pressure is known as the "Langevin acoustic radiation pressure" (ARP). The invention lies in the use of the forces imposed by the application of this pressure to deflect the cantilever of a probe-based instrument. One such probe 112 is illustrated schematically in FIG. 3A. The probe 112 includes a cantilever 122 and a tip 124 mounted or otherwise provided on a free end of the cantilever 122. The ARP is related to the average energy density, U, at the target surface and it may if desired be localized at a specific location on the cantilever 122 by placing that location of the cantilever 122 at the focal plane of an acoustic lens. As a simple model based on plane waves, it can be assumed that, at the focal plane, a time harmonic acoustic pressure wave of amplitude, $P_i$, is normally incident on a cantilever immersed in a liquid and that the wave is reflected with a complex pressure reflection coefficient, ?, at an angular frequency, $?=2\pi f$. This reflection coefficient can be considered as a weighted average over the incident spectrum of plane waves that would be included in a focused beam. In this case, the time-averaged energy density at the cantilever surface will be given by $$U = \frac{P_i^2}{2\rho c^2}(2|\Gamma|^2) \qquad \text{Equation (1)}$$

where ? is the bulk density of fluid, c is the speed of sound in the liquid and |G| denotes the absolute value of the reflection coefficient. Using the relation that the average intensity of the incident beam is given by $I_i = P_i^2/(2?c)$, the Langevin radiation pressure on the cantilever 122, O, can be expressed in terms of the intensity as $$\Omega = \frac{I_i}{c}(2|\Gamma|^2) \qquad \text{Equation (2)}$$

The total force applied to the cantilever in the direction of propagation of the incident wave can be found by integrating the radiation pressure. Accordingly, the total applied force is proportional to the average power incident on the cantilever 122. Note that the discussion above neglects the absorption of the ultrasonic energy in the beam and in the fluid medium. In case of absorption in the fluid medium, acoustic streaming can be induced. The fluid flow induced by this mechanism can generate additional forces on the cantilever. The losses in the cantilever are generally very small and hence can be neglected. Also note that Equations 1 and 2 apply to cantilever actuation applications in air. Since the velocity of sound in air is approximately 330 m/s and |G|~1, the same amount of force can be applied to the cantilever with $\frac{1}{5}^{th}$ of the acoustic power. The high attenuation of ultrasonic waves in air may limit the frequency of operation.

The localization of the radiation force can be estimated using the relations for diffraction limited focused acoustic beams. For an acoustic lens with an F-number equal to one, the 3-dB diameter, $d_s$, of the diffraction limited beam at the focal plane is given by the relation d~1.02?, where ? is the wavelength of the time harmonic acoustic wave in the fluid. For example, in water (c~1.5×10³ m/s), the diameter of the beam at the focal plane will be between 5 µm to 10 µm when the RF drive frequency, f is in the 150–300 MHz range. According to Equation 2, for 150 µW incident average acoustic power at the focal plane of the lens, $P_i = \pi d^2 I_i/4$, the force applied to the AFM cantilever will be 145 nN, assuming perfect reflection at the water/cantilever interface (|?|=1). Both these frequency and power levels are typically used for acoustic microscopy and acoustic ink printing applications.

It has been discovered that two separate high frequency beams with slightly different frequencies can be used to generate radiation pressure at the difference frequency to generate elasticity images. The acoustic radiation pressure field can be localized by intersecting the high frequency beams at the desired location. This results in an effective amplitude modulation. It has also been discovered that modulated sonic beams can be used to generate acoustic forces to image mechanical properties of a variety of objects with high spatial resolution. These uses are discussed, for example, in: M. Fatemi and J. F. Greenleaf, "Ultrasound-stimulated vibro-acoustic spectrography," *Science*, 280, pp. 82–5, 1998; U.S. Pat. No. 5,991,239, Confocal Acoustic Force Generator; U.S. Pat. No. 5,921,928, Acoustic Force Generation by Amplitude Modulating a Sonic Beam; and U.S. Pat. No. 5,903,516, Acoustic Force Generator for Detection, Imaging, and Information Transmission Using the Beat Signal of Multiple Intersecting Sonic Beams.

B. Experimental Embodiment

Figure 3B:
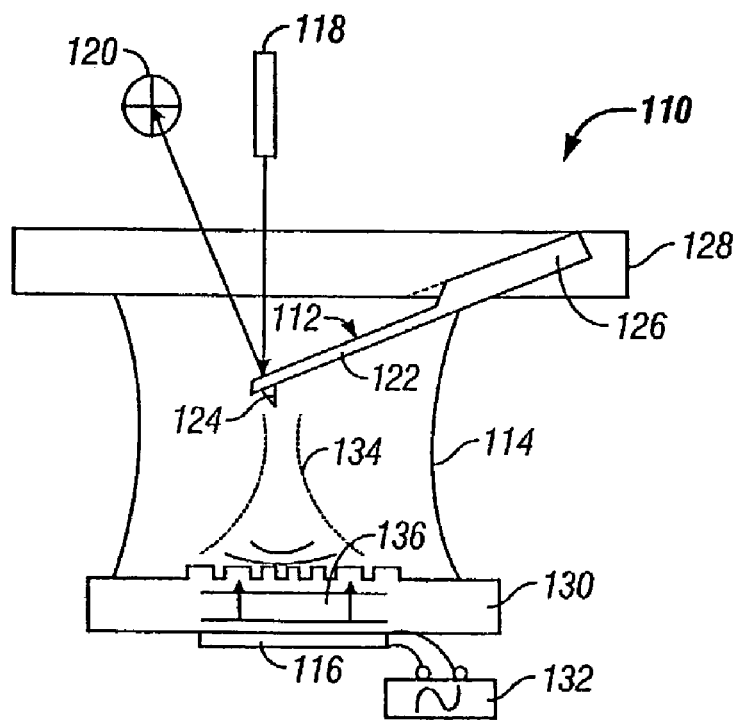
FIG. 3B schematically illustrates an ultrasonically actuated AFM constructed in accordance with a first embodiment of the present invention and incorporating the ARP deflected cantilever of FIG. 3A and an associated ultrasonic actuator.

Referring to FIG. 3B, a possible AFM for deflecting a cantilever by focusing ultrasonic energy in the manner described above is illustrated at 110. The AFM 110 includes the probe 112 described above in conjunction in FIG. 3A (the probe 112 is configured to operate in a liquid contained within a cell 114), an ultrasonic actuator 116 for generating ARP, and a detector 118, 120. As discussed above, the probe 112 includes a cantilever 122 and a tip 124 mounted or otherwise provided on a free end of the cantilever 122. The cantilever of this example is made of silicon and has a spring constant of 0.148N/m and a fundamental resonance around 4.6 kHz in water. The base of the cantilever 122 is fixed to an optically transparent probe support 126, which may fit into a commercial AFM scanhead 128. The fluid cell 114 is positioned beneath the scanhead 128 with the probe 112 located by it. (Relative positional terms such as "above", "beneath" "in front of" "behind," "horizontal," "vertical," etc. are used by way of reference for simplicity sake and are in no way limiting.) An ultrasonically transparent substrate 130, preferably made of a hard substrate like glass or silicon, is placed below the probe 112 and supports fluid cell 114. The ultrasonic actuator 116, which is preferably formed from a zinc oxide (ZnO) transducer, is mounted on the bottom of the substrate 130. Alternatively, the ultrasonic actuator can be placed on the side of the substrate directly facing the cantilever. The ultrasonic transducer can be shaped as a focusing device and electrically isolated from the fluid environment, removing the need for an ultrasonically transparent substrate. The ultrasonic actuator 116 is driven by a RF signal generator 132 to generate a beam 134 that deflects the cantilever 122 away from the substrate 130. The RF signal generator 132 has an optional modulation input that allows the amplitude of the RF signal to be varied with time. The modulation signal may be a square wave, a sinusoidal wave, a triangle wave or an arbitrary time-varying modulation. The RF signal generator also has an input or an internal adjustment that allows control over the baseline (unmodulated) power of the RF signal. The scanhead 128 may include an XY actuator and a Z actuator to permit the probe 112 to scan a sample in the fluid cell 114. Alternatively, the scanhead 128 could be stationary, and the substrate 130 could be driven to scan relatively to the scanhead 128. Detector 118, 120 detects cantilever deflection during scanning. The detector includes a laser 118 positioned above the cantilever 122 and a four-quadrant photodetector 120 configured to receive laser light reflected from the upper surface of the cantilever 122. As is conventional, signals from the photodetector 120 can be used as feedback to control operation of the RF signal generator 132 to maintain a desired characteristic of cantilever deflection, such as magnitude, and/or phase during scanning.

The substrate 130 of this embodiment contains a surface micromachined acoustic Fresnel lens 136 that serves as the focusing device in the illustrated embodiment. The illustrated lens structure is part of a 2-D array of micromachined acoustic lenses on the same glass plate. Lenses of this type were originally developed for acoustic microscopy and ink printing purposes and are well known. The Fresnel lens 136 of this embodiment is preferably designed such that, when the zinc oxide transducer 116 is excited with a sinusoidal drive signal at a frequency equal to about 179 MHz, the ultrasonic beam 134 will be focused to a diameter of approximately 5 μm to 10 μm at a focal distance of 360 μm. The 5 μm minimum diameter is even smaller than the 8 μm to 12 μm diameter of most laser beams. As a result, the lens 136 can be used to apply a pinpoint force to the free end of the cantilever 122 or any other point of interest along the length of the cantilever 122. Of course, the focal length of the Fresnel lens can be varied to accommodate any physical design constraints to place the ultrasonic actuator further or closer from the cantilever. Other types of acoustic lenses may also be used to shape the beam. A wide variety of acoustic lenses and beam shaping devices have been developed for medical ultrasound applications (phased arrays), scanning acoustic microscopy, acoustic printing and related techniques. For example, a simple hemispheric cutout in the surface of the substrate 130 will form an acoustic lens that will focus the outgoing beam. Further, materials with different speeds of sound may be patterned on top of the acoustic actuator to shape the profile of the outgoing beam. Further, the electrodes on the ultrasonic actuator may be patterned to form focused and/or steered beams using techniques such as Fresnel zone plates.

C. Characteristics of an Ultrasonically Driven Cantilever

Figure 4:
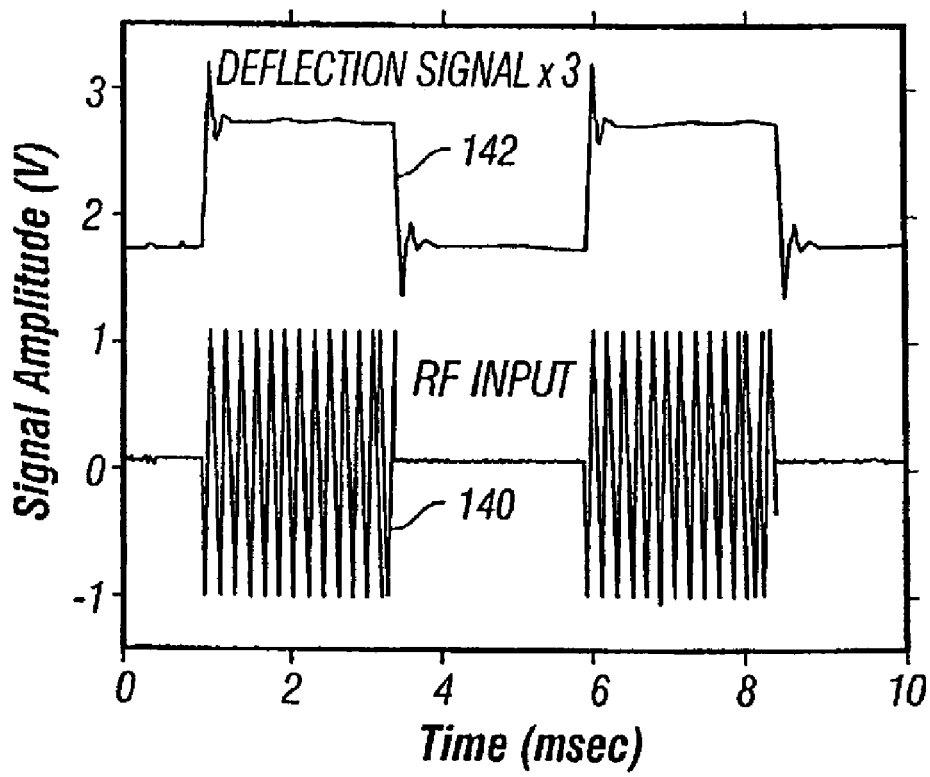
FIG. 4 is a graph illustrating signal amplitude versus time of both drive input and measured cantilever deflection of the instrument of FIG. 3B.

Applying an RF drive voltage to the ZnO transducer 116 deflects the cantilever 122 in the manner illustrated in FIG. 4, which plots the RF signal input to the ultrasonic transducer and the resulting cantilever deflection via the curves 140 and 142, respectively. To obtain this data, the cantilever 122 of FIG. 3B was positioned on or near the focal plane of the ZnO transducer 116 using the Z-actuator of the scanhead 128. The X-Y actuator in the scanhead 128 was then driven to move the cantilever 122 in the X-Y (horizontal) plane to bring the tip 124 generally to the focal spot of the acoustic beam 134. The Z actuator was then driven to move the cantilever 122 vertically to obtain maximum cantilever deflection for a prevailing RF generator setting. The RF signal's amplitude was then modulated to 200 Hz at a frequency of about 179 MHz by a 50% duty cycle square wave with a 5 msec period. Then, after a transient dominated by its fundamental resonance in water, the cantilever 122 was driven upwardly away from the substrate 130, exhibiting a step response as represented by the curve 142 in FIG. 4. The particular response reflected by the curve 142 is consistent with the fact that the cantilever 122 of this exemplary embodiment has a fundamental resonance around 4.6 kHz in water. Corresponding data obtained from different cantilevers would produce curves of different magnitude and spacing but similar shape. The low frequency appearance in the RF drive signal curve 140 is due to the "aliasing" from the relatively low sampling rate of the digital oscilloscope (100 kS/s) used to obtain the data reflected in FIG. 4. The high signal-to-noise ratio obtained in the waveforms indicated by the curve 140 shows the potential of the method of surface characterization.

As should be apparent from above discussion, the force imposed by the ZnO transducer 116 is unidirectional. As a result, the ultrasonic beam 134 cannot pull the cantilever 122 toward the transducer 116 but, instead, can only "push" the AFM cantilever 122 in the propagation direction. If the designer wanted to configure the AFM 110 to selectively pull the cantilever 122 toward the substrate 130 rather than push it away from the substrate, the cantilever 122 could be manufactured with a bias that maintains it in contact with the substrate 130 in the absence of a drive signal to the RF signal generator 132. The RF signal generator 132 could then be driven to overcome the bias and push the cantilever 122 from the substrate 130. The drive voltage could then be reduced to permit the cantilever 122 to move towards the substrate 130, hence, in effect, pulling the cantilever 122 towards the substrate 130. Alternatively, in some configurations, an ultrasonic actuator could be placed both above and below the cantilever to push from both sides.

The previous paragraph demonstrates a very important capability of the current invention. The ultrasonic cantilever actuator can independently control both the DC and AC forces applied to the cantilever over an extremely wide bandwidth. This opens up a large range of applications for this actuator. One example is an imaging method called Force Modulation. In this method, an AFM tip is brought into contact with a sample surface and then an AC modulation force is applied to the cantilever. The detector then measures the amount of AC deflection of the cantilever. On hard samples, the cantilever cannot indent into the surface, and no deflection is detected. On softer samples, the ultrasonic modulation force causes the tip to indent into the sample, resulting in a measurable AC deflection of the cantilever. Separate control over the DC force allows control over the tracking force that the AFM system uses to maintain contact between the tip and the surface.

The RF voltage can also be varied slowly to permit a quasistatic measurement to be performed. A quasistatic force imposition process is considered to be one in which, if the forces were to be removed at any stage during the process, system would be in equilibrium from that time on. Hence, the RF voltage can be changed slowly enough to maintain equilibrium while the voltage is being altered. This procedure is in contrast to a dynamic (AC) measurement in which the RF signal is modulated at a high frequency and the system requires time to stabilize when force adjustment terminates. The cutoff between quasistatic and dynamic measurements is usually considered to be a frequency value below the cantilever's fundamental resonant frequency.

Figure 5:
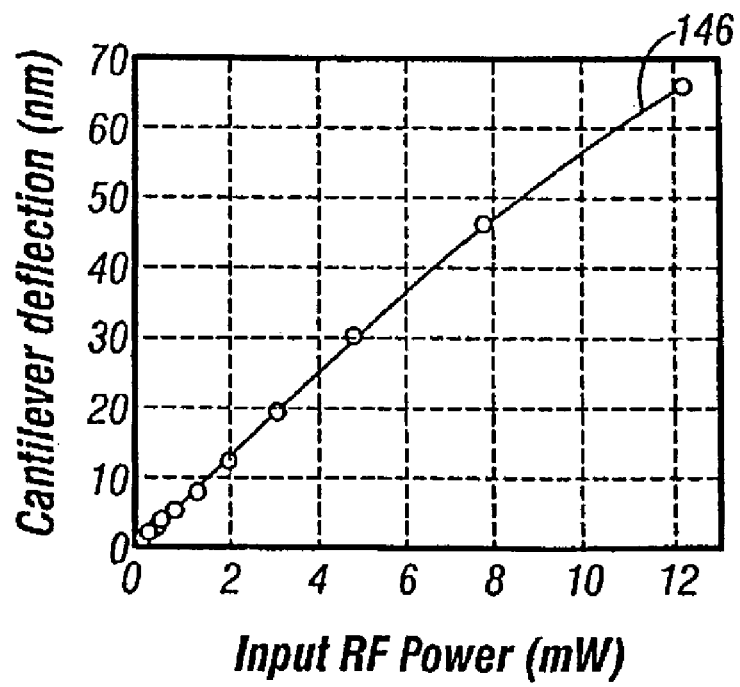
FIG. 5 is a graph of cantilever deflection versus input power for the instrument of FIG. 3B.

The force applied to the cantilever 122 is also proportional to the magnitude of the drive voltage applied to the RF signal generator 132. This relationship is illustrated by FIG. 5, the curve 146 of which traces measured cantilever deflection as a function of the input RF voltage to the ZnO transducer 116. The cantilever used to obtain this data was a 205 μm thick, 2 μm thick, 29 μm wide, and had a spring constant of 1.14N/m. As expected from Equation 2 above, the curve 146 indicates that the radiation force on the cantilever 122 varied generally linearly with input power to the transducer 116 over a wide operating range.

The generally linear relationship between drive voltage and cantilever deflection can be relied upon to calibrate the force applied to the cantilever for a particular drive voltage if the spring constant of a reference cantilever is known. For example, in the graph of FIG. 5, a cantilever deflection of 31 nm was measured when 4.98 mW was input to the ZnO transducer. In an experiment using the data, the cantilever was assumed to have a spring constant of 1.14N/m. That assumption would be verified if a force of 35 nN would have to be applied to the free end of the cantilever to deflect it. An independent measurement of the insertion loss of the acoustic transducer and lens combination was performed to determine the incident acoustic power at the cantilever surface. This measurement yielded loss of 26.5 dB. Therefore, for the 4.98 mW electrical power on the ultrasonic transducer, the incident acoustic power on the tip was determined to be 11.1 μW. Using Equation 2, the force on the cantilever due to acoustic radiation pressure was predicted to be 13 nN, assuming an average reflection coefficient 0.85 for the 2 μm thick cantilever immersed in water. This number is in the same order of magnitude as the value predicted from the cantilever deflection. The calibrated force was then used to measure the spring constants of 405 and 105 μm long cantilevers on the same chip. The measured values were 0.132N/m and 10.18N/m, respectively. These values were 12% smaller and 19% larger, respectively, than the corresponding values quoted by the vendor.

The spring constant of a cantilever can be also determined without directly calibrating force by comparing the deflection of the cantilever at a particular drive voltage to the deflection of a reference cantilever of known spring constant at the same drive voltage. Specifically, the deflection of a reference cantilever of a known spring constant can be measured at one or more drive voltage(s), and the reference cantilever can then be replaced with one of an unknown spring constant. The same drive voltage(s) can be supplied to the RF signal generator 132, and the cantilever's deflection can be measured at the drive voltage(s). The cantilever's spring constant can then be determined simply by determining the ratios of the two deflections at the same drive voltage.

Cantilever spring constants may also be determined dynamically, by ramping the ultrasonic force up and down. In this case, the spring constant of the cantilever is related to the slope of the cantilever deflection versus ultrasonic drive voltage. Since this is an AC measurement, this method has the advantage of being less sensitive to DC drift in the deflection of the cantilever or drift in the detection system due to changes in temperature.

The proportional relationship between cantilever deflection and drive voltage magnitude can also be used to obtain useful information concerning a sample. For instance, the RF signal generator 132 of FIG. 3B can be controlled to generate force curves. Force curves are often used to provide an indication of the magnitude of force required to obtain an effect such as indenting a sample surface, breaking the binding molecules between a sample and a probe in contact with the sample, etc. In order to generate a force curve with prior instruments, it was necessary to actuate a Z actuator in the scanhead to drive the probe against the sample (or move it away from the sample). The same effect can be obtained using an ultrasonic actuator simply by modulating the drive signal to an RF signal generator or other power source until the desired effect is achieved. The known proportional relationship between the signal drive voltage and cantilever deflection can then be used to calculate the force. No actuation of a separate Z actuator is required.

Figure 6:
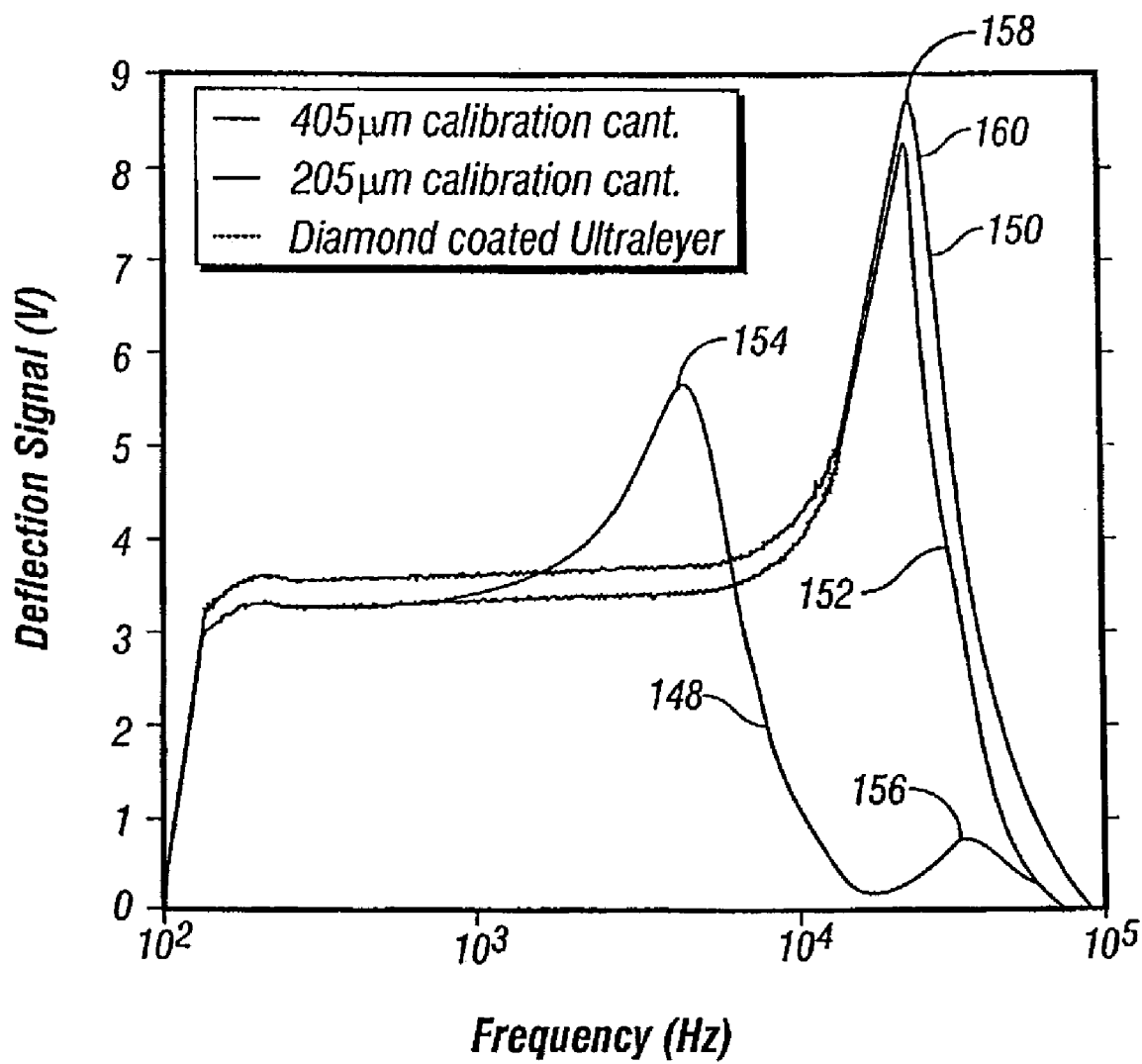
FIG. 6 is a graph of deflection versus frequency of various cantilevers usable in the system of FIG. 3B.

AFM cantilevers can also respond dynamically to radiation pressure, and those dynamic responses can be measured. Specifically, time harmonic forces can be generated by applying a sinusoidal amplitude modulation on the RF input signal. By choosing the modulation factor to be less than one, an appropriate biasing force can be applied to actuate the cantilever at the modulation frequency and its second harmonic. The deflection of the cantilever can then be recorded e.g., by using a lock-in amplifier, which uses the modulation signal as its reference input and locks to the modulation frequency. The normalized magnitude of the lock-in amplifier, was output as a function of the modulation frequency for a 405 μm calibration cantilever, a 205 μm calibration cantilever, and a V-shaped, diamond coated force modulation cantilever. That output is plotted in the curves 148, 150, and 152 respectively in FIG. 6. (The frequency sweep for this example was limited to 0.2–100 kHz range due to short time constant and the limitations of the lock-in amplifier.) The points 154 and 156 on curve 148 reveal that the fundamental and second modes of the long cantilever are about 4.6 kHz and 38 kHz, respectively. The points 158 and 160 on the curves 150 and 152 indicate that the short reference cantilevers and force modulation cantilever both resonate at about 25 kHz. The curves 148, 150, and 152 of FIG. 6 also show that the radiation pressure method of cantilever deflection can be used to actuate different cantilevers without any undesired effects of the cantilever support and the fluid cell. It has to be noted that, although only the flexural modes of the cantilevers are excited in this example, torsional modes of the cantilever can also be characterized by applying the radiation pressure at off-axis locations on the cantilever.

Figure 1A:
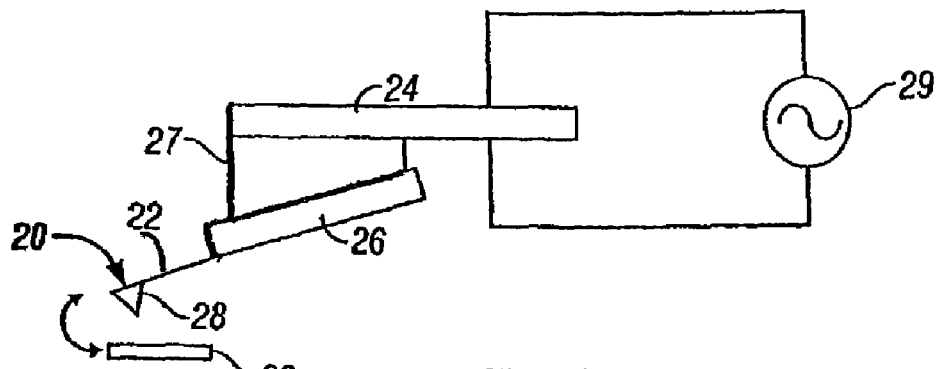
FIG. 1A is a schematic view of a conventional AFM having a piezoelectric drive, appropriately labeled "prior art"
Figure 1C:
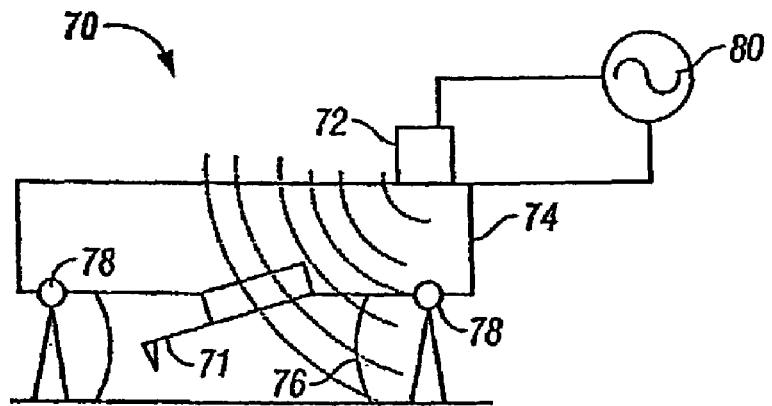
FIG. 1C is a schematic view of a conventional acoustically driven microscope, appropriately labeled "prior art"
Figure 7B:
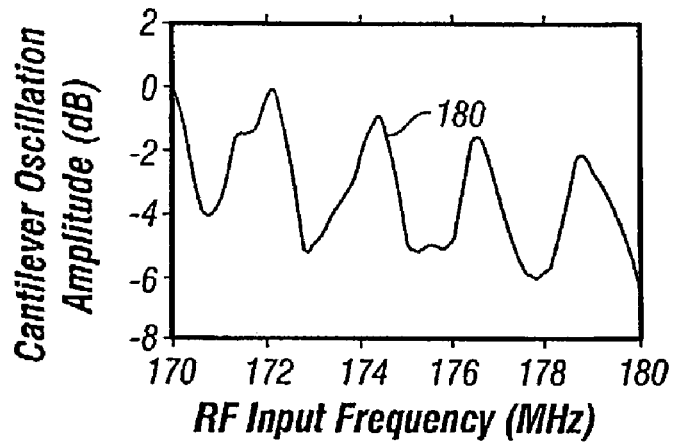
FIG. 7B is a graph illustrating the response of the cantilever of the system of FIG. 3B to changes in RF input frequency.

The relative ease with which both a resonance peak of an oscillation cantilever can be identified is confirmed with reference to FIG. 7A, which plots RMS deflection vs. drive frequency for a relatively short, thick cantilever (having a length of about 100 μm and a thickness of about 700 μm that is excited alternatively via an acoustic drive of the type illustrated in FIG. 1C and an ultrasonic drive of the type illustrated in FIG. 3B, respectively. The true response of the cantilever at rest, as determined via a known thermal tuning technique, is reflected by the curve 162. Point 164 of curve 162 indicates that the cantilever actually experiences a fundamental resonance at about 15 kHz. Curve 166 indicates that it is virtually impossible to differentiate the cantilever resonance from other, parasitic resonances when the cantilever is driven by a conventional acoustic drive.

In sharp contrast, the cantilever resonance can be clearly detected at point 170 in curve 168. This effect is believed to be due at least in part to the fact that the ZnO transducer 1) acts along the length of the cantilever and, therefore has high gain, and 2) acts at least primarily on the cantilever rather than other components of the system and, accordingly, induces far fewer and smaller-amplitude parasitic resonances.

The measured response to ultrasonic excitation as reflected by the curve 168 in FIG. 7A is a true response at the excitation amplitude imparted by the ZnO transducer. The frequency shift between the peaks 164 and 170 of curves 162 and 168 results only from the known effects of finite excitation amplitude, not any measurement error. Hence, exciting the cantilever with an ultrasonic actuator permits the response of the cantilever to a given RF voltage to be anticipated with great confidence, even when the probe is operated in a liquid. Measurements can therefore be taken using cantilever/medium combinations that were heretofore not possible.

Figure 1D:
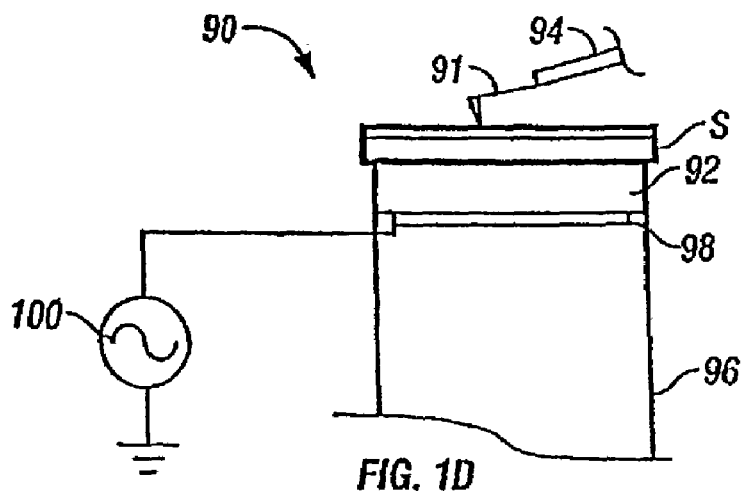
FIG. 1D is a schematic view of a conventional ultrasonic force microscope (UFM), appropriately labeled "prior art"
Figure 1B:
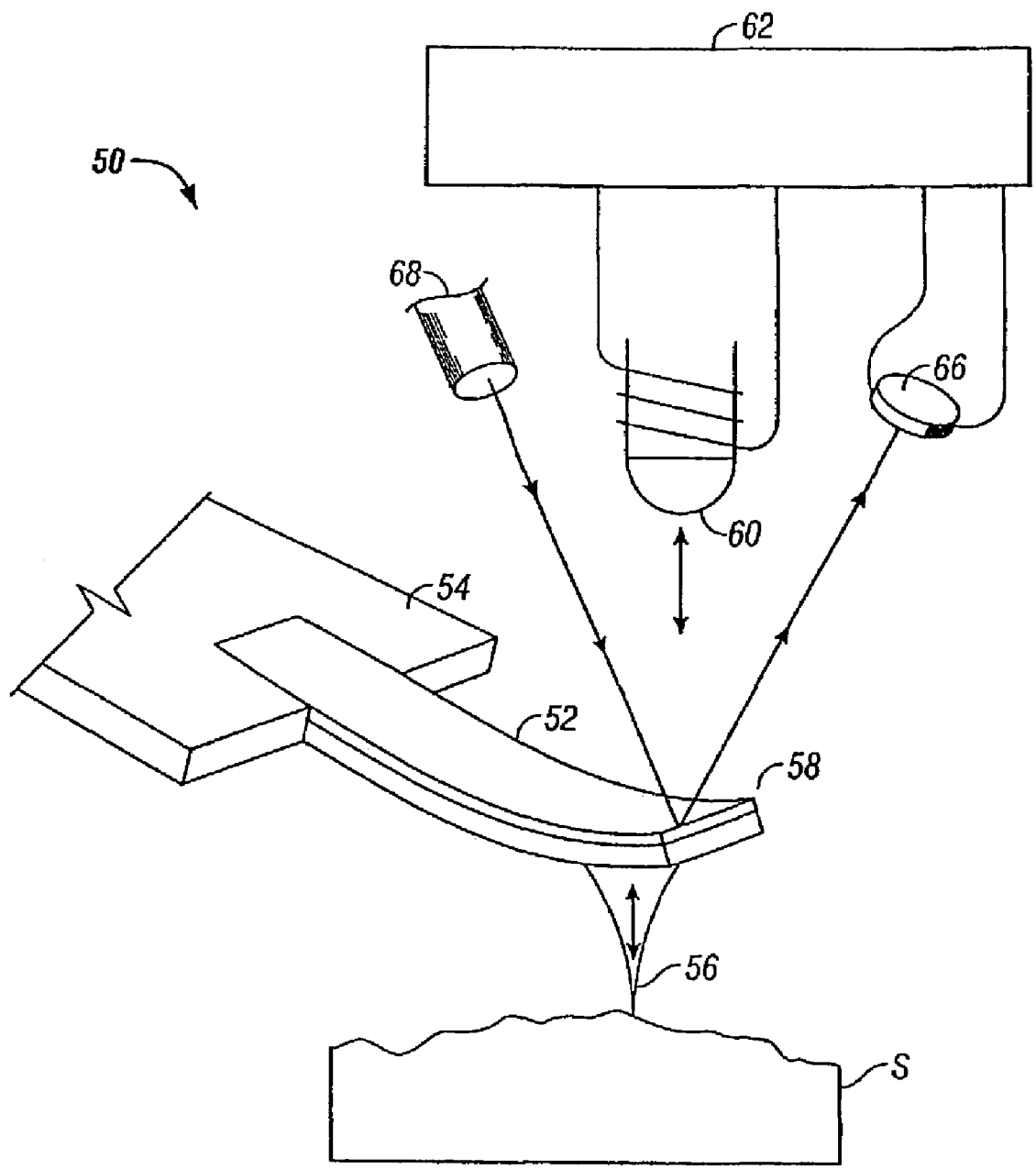
FIG. 1B is a schematic view of a conventional magnetic drive system, appropriately labeled "prior art"
Figure 2A:
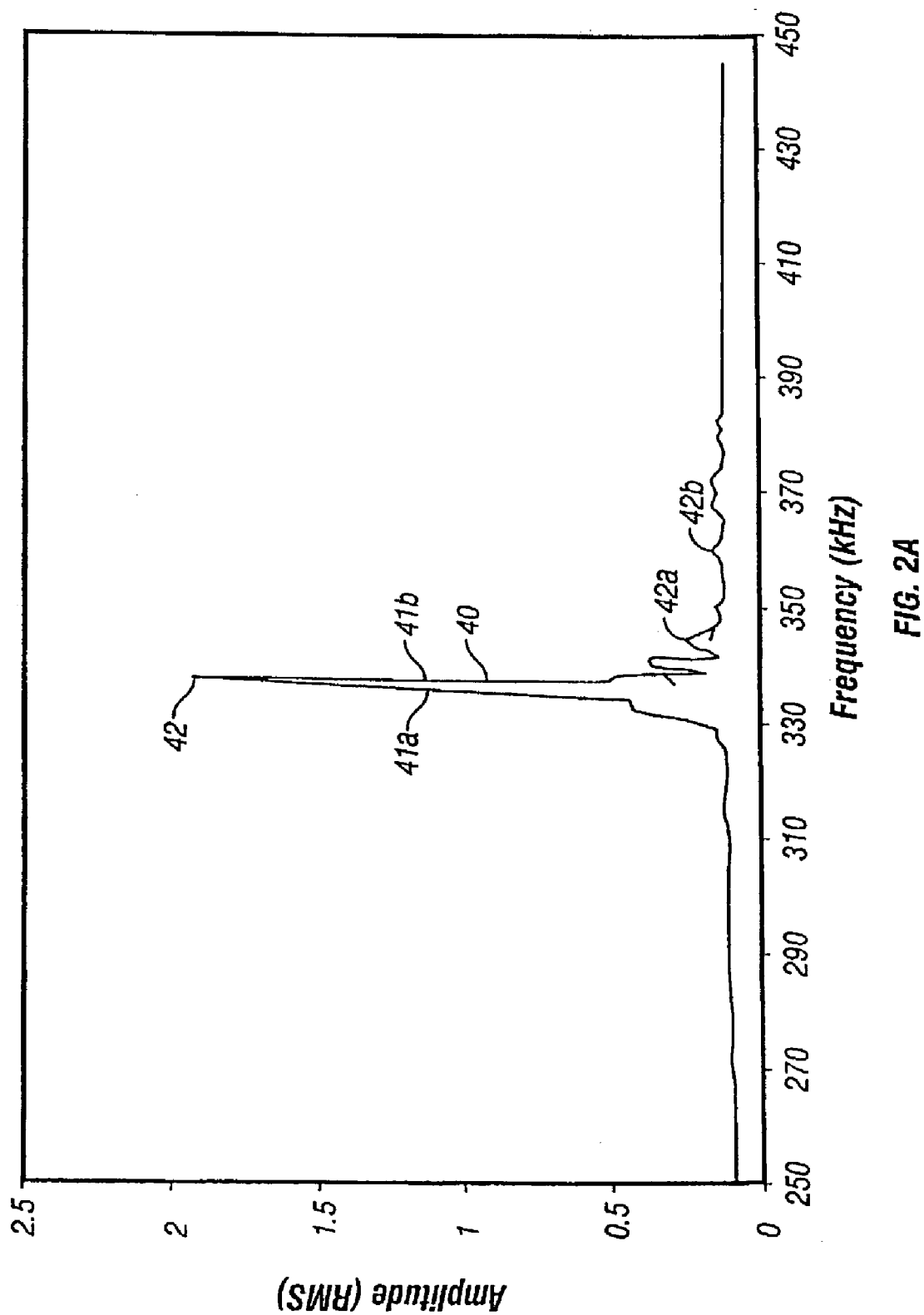
FIG. 2A is a graph illustrating the response of a typical AFM to an oscillating excitation when the cantilever is operating in air.
Figure 2B:
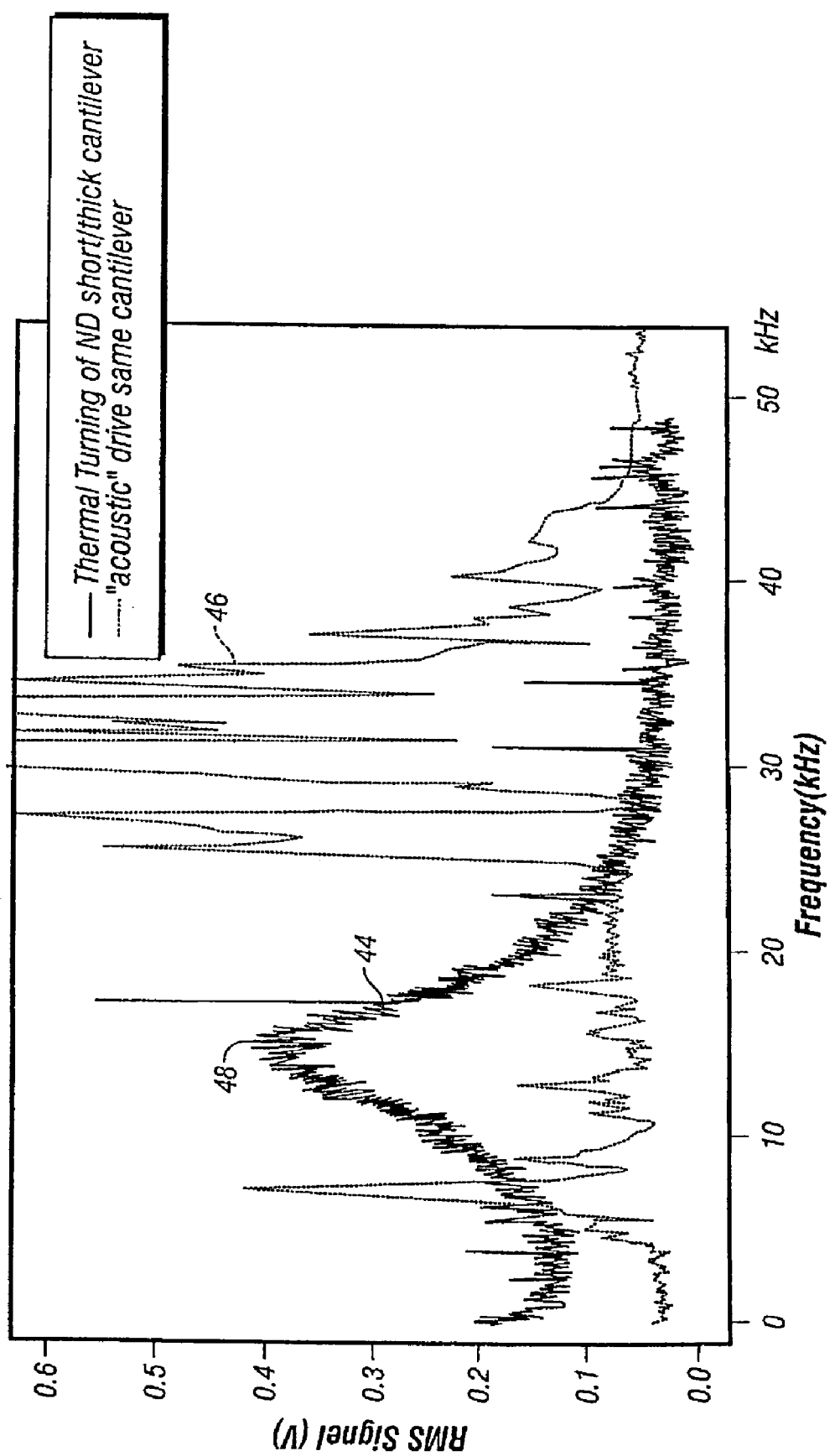
FIG. 2B is a response of a typical AFM cantilever to oscillating excitation when the cantilever is operating in a liquid.

It has been discovered that an ultrasonic-actuator based system has a very wide bandwidth for exciting the cantilever. The inventors have performed experiments where the RF excitation signal is modulated at frequencies of more than 5 MHz, allowing unprecedented bandwidth for cantilever actuation as demonstrated by the curve 180 in FIG. 7B, which plots cantilever oscillation amplitude as a function of RF frequency at a 200 Hz modulation rate. In practice, it is possible to modulate the RF signal up to about $\frac{1}{10}$ of the RF signal frequency or even higher. For a 300 MHz RF frequency, a cantilever actuation bandwidth of even 30 MHz is realizable. In fact, it is believed that the RF frequency from a low of 10 MHz or possibly even lower for air applications to 1 GHz or even higher for water applications with surface micromachined cantilevers for which attenuation may not be a problem. This cantilever actuation bandwidth is much greater than is provided by any other AFM cantilever actuators, particularly acoustic and magnetic drives of the type illustrated in FIG. 1C or ultrasonic force actuators of the type illustrated in FIG. 1D. An AFM having an ultrasonically driven cantilever can therefore be used to scan at rates that would have heretofore been considered outrageously fast. It also permits dynamic experiments to be conducted in which the probe repeatedly interacts with the sample surface at very high frequencies.

D. Tapping Mode Embodiment

An ultrasonic actuator of the type described above can be used to drive an AFM cantilever to oscillate at virtually any desired frequency significantly below the RF carrier frequency. An ultrasonic actuator therefore can be directly used as TappingMode actuator in an AFM. A TappingMode AFM 210 using an ultrasonic actuator is shown schematically in FIG. 8. As with the more theoretical embodiment of FIG. 3B, the instrument 210 includes a conventional probe 212, an ultrasonic actuator 216, and a detector 220. The probe 212 is configured to operate in a fluid cell 214 containing a sample S. It includes a cantilever 222 having a base affixed to a support 226 and a free end bearing a tip 224. Also as in the embodiment of FIG. 3B, an ultrasonically transmissive substrate 230 is placed below the cantilever 222. A focusing device such as a Fresnel lens (not shown) may, if desired, be placed on or in the substrate 230. The ultrasonic actuator 216 is mounted on the bottom of the substrate 230 and powered by an RF signal generator 232 under the control of an AFM controller 238. The RF signal generator 232 produces an RF oscillation in the ultrasonic actuator 216 and then modulates the amplitude of that signal in response to a TappingMode drive signal as supplied by the controller 238. The controller 238 may turn the drive signal on and off with a square wave such as the one illustrated in FIG. 4, or it could modulate the amplitude of the drive signal in proportion to that sine wave. The controller 238 also drives an XYZ actuator in the scanhead 228 in the conventional manner.

The traditional TappingMode piezoelectric drive may be taken out of the loop and replaced by the ultrasonic actuator 216. In this case, the RF drive signal described in the preceding paragraph would always be used to drive the ultrasonic actuator 216. In the preferred embodiment however, a piezoelectric drive 240 can be retained, and a suitable switch 242 can be provided to permit a drive signal to be selectively transmitted to either modulate the output of RF signal generator 232 and hence activate the ultrasonic actuator, or the drive signal can be sent to the piezoelectric drive 240 directly from the AFM controller 238. For example, the resulting instrument could be operated in either air or liquid, with the piezoelectric drive 240 being used to effect operation in air and the ultrasonic actuator 216 being used to effect operation in liquid.

E. Overhead Ultrasonic Actuator Embodiment

Figure 8:
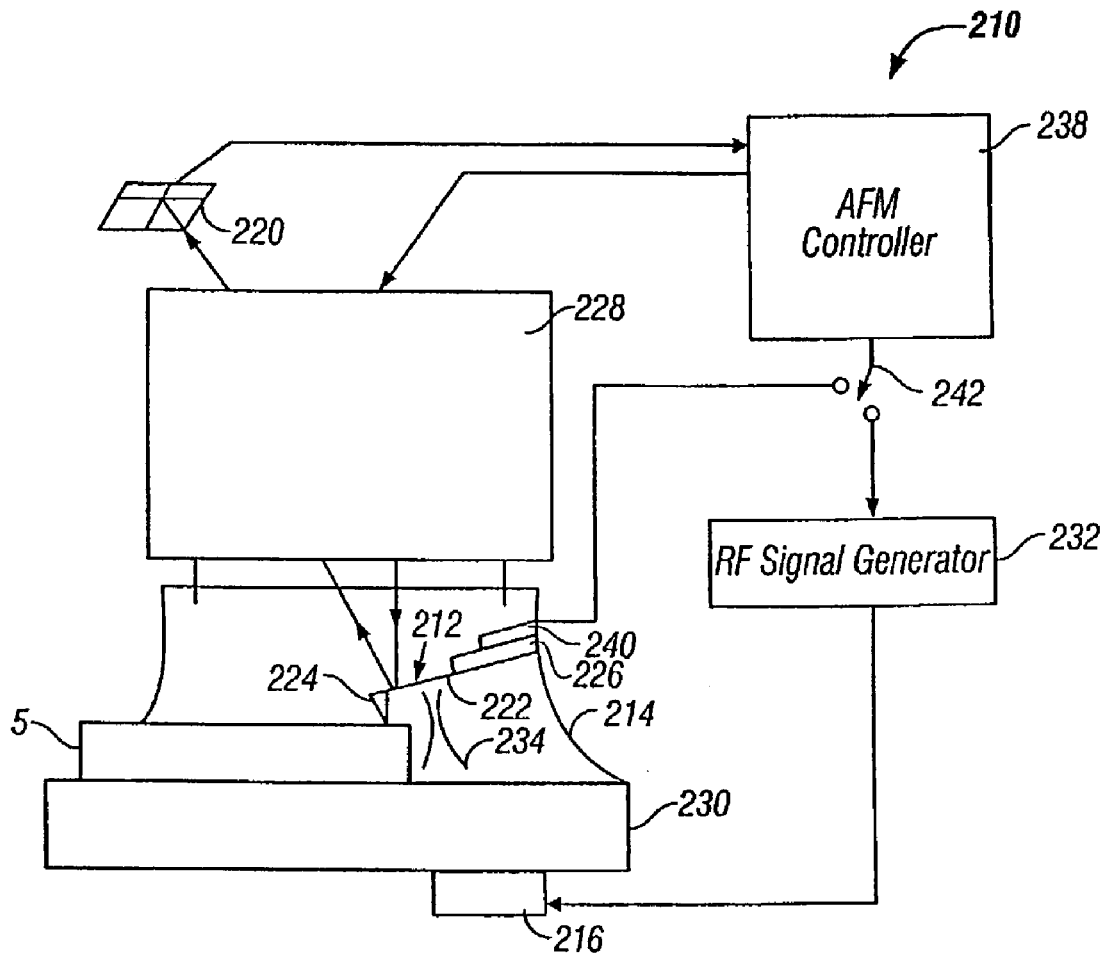
FIG. 8 schematically illustrates an ultrasonically actuated AFM constructed in accordance with a second embodiment of the invention in which the AFM is configured for an oscillating mode of operation.
Figure 9:
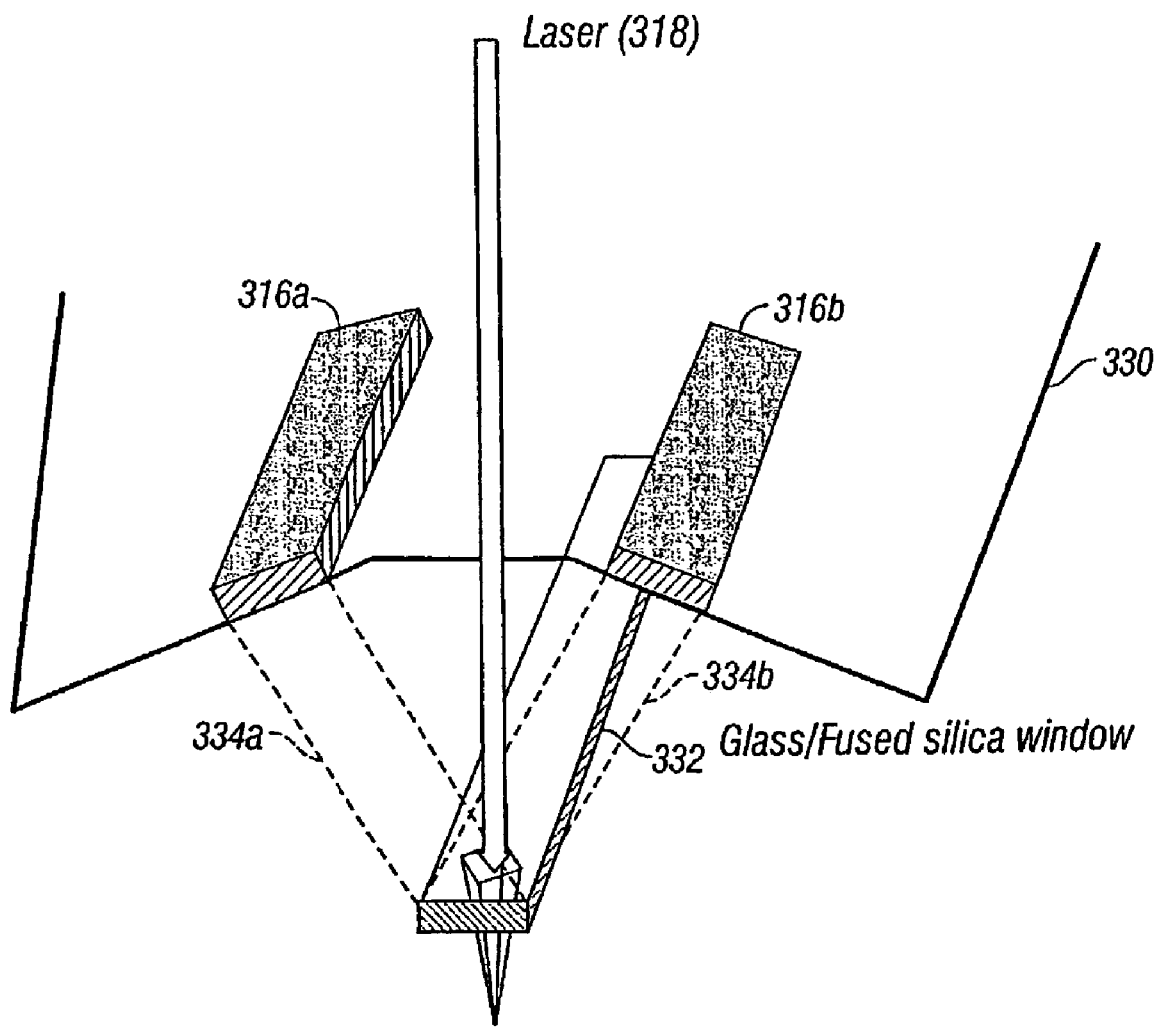
FIG. 9 is a schematic top plan view of the ultrasonic drive for an AFM constructed in accordance with a third embodiment of the invention in which the ultrasonic actuator and detector are positioned on a common side of the cantilever opposed to the sample supports.

A limitation of the instruments illustrated in FIGS. 3B and 8 is that the sample must be ultrasonically transmissive to permit unfettered transmission of the ultrasonic beam from the ultrasonic actuator, through the sample, and to the cantilever. A more versatile ultrasonic actuator assembly is schematically illustrated in FIG. 9. In this embodiment, at least one ultrasonic actuator is mounted on a holder 330 positioned above the cantilever 322. The holder 330 is also positioned between the cantilever 332, on the one hand, and a laser 318 and photodetector (not shown), on the other hand. The holder 330 may be constructed of glass or any another material that is transparent to light and transmissive to ultrasonic energy. In the illustrated embodiment, two ZnO or other piezo electric transducers 316*a* and 316*b* are mounted on the holder 330 on opposite sides of a vertical plane laterally bisecting the cantilever 322, and the relevant portions of the holder are inclined to direct the corresponding ultrasonic beams 334*a*, 334*b* at the lateral centerline of the longitudinal centerline of the cantilever 322. However, a single ultrasonic transducer would suffice in many applications. A Fresnel lens or other focusing device (not shown) could be formed in or mounted on the holder 330, if desired. The holder, ultrasonic actuator(s), and associated components of this embodiment could also be used in place of the corresponding components of the embodiments of FIGS. 3B and 8, widening the range of applications of those embodiments.

F. Cantilever Characterization and Mode Shape Imaging

Figure 10A:
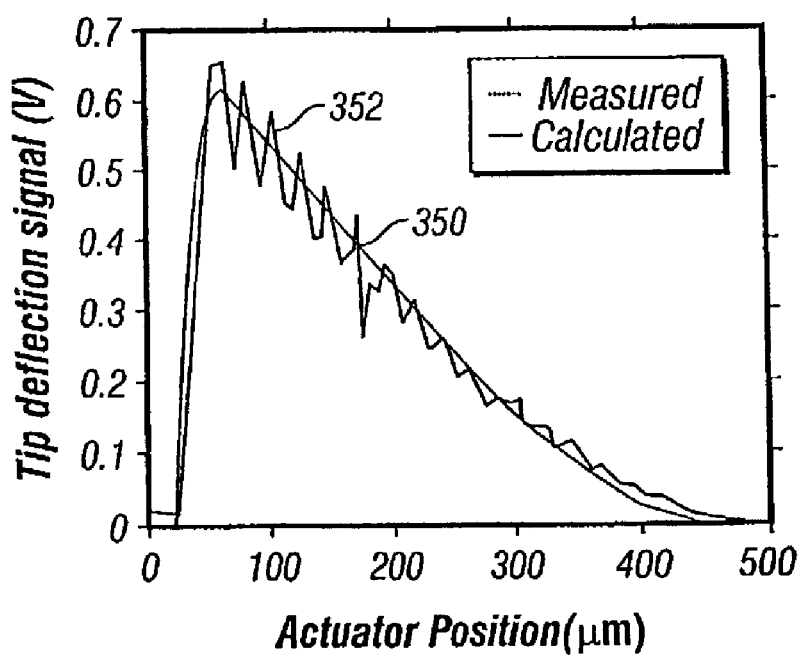
FIG. 10A is a graph of probe tip deflection versus beam impingement position for low frequency excitation of the cantilever of the instrument of FIG. 8.

One of the unique features of an ultrasonic actuator is that it can produce a localized force at the desired location on the cantilever. It is therefore possible to very precisely control the vibration of a cantilever and to excite more flexural and torsional modes in the cantilever. These effects are illustrated in FIG. 10A, in which calculated and measured curves of the mode shape of a 450 μm cantilever in the AFM of FIG. 8 are shown at 350 and 352, respectively. The data was taken at an excitation frequency of 1.5 kHz, which corresponds to the first resonance mode of this cantilever in water. As one would expect, the curves 350 and 352 reveal that cantilever deflection is maximized when the ultrasonic energy is directed at the free end of the cantilever and decreases when the focus point moves progressively toward the base. Stated another way, exciting the cantilever in its first resonance mode produces a single deflection peak.

Figure 10B:
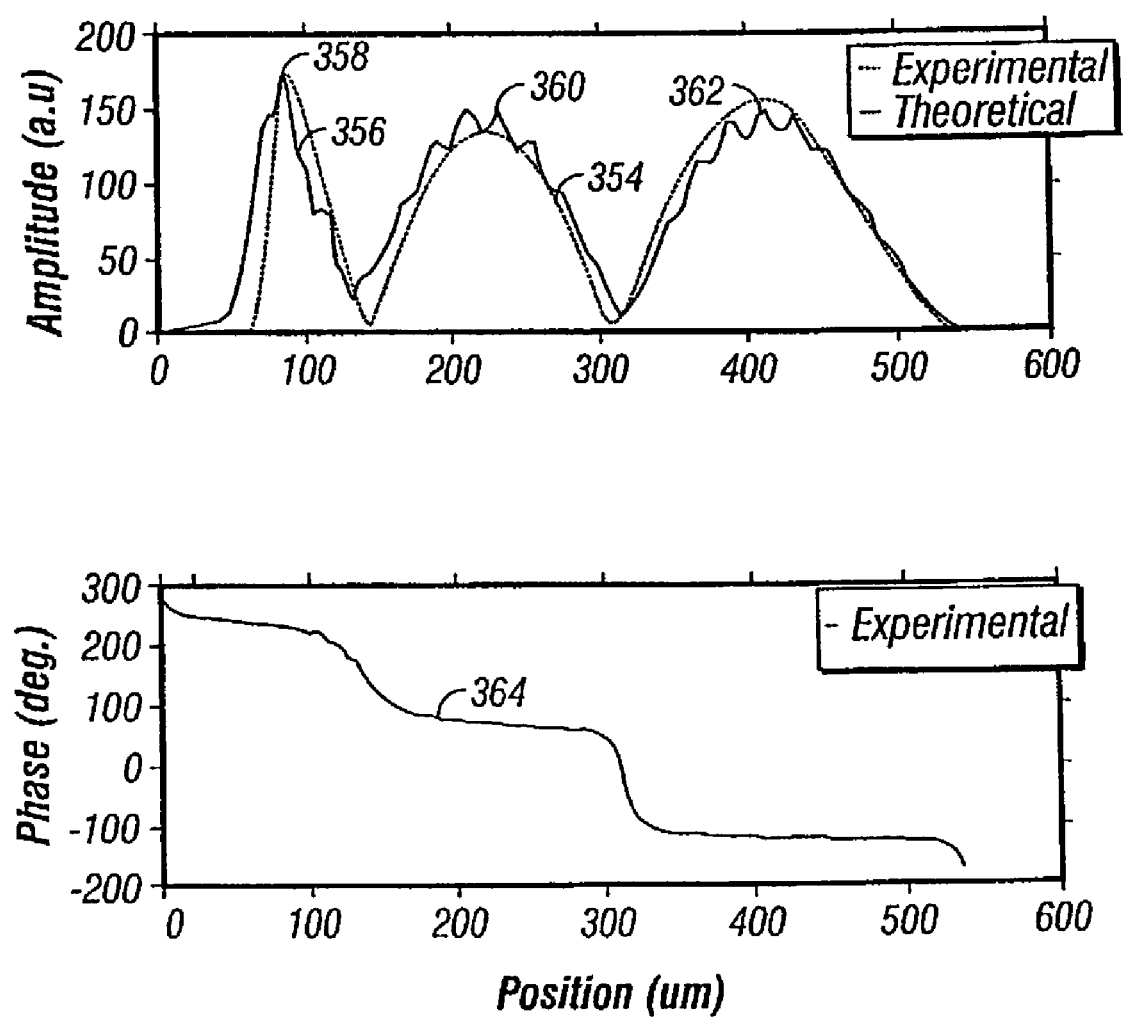
FIG. 10B is a graph of probe tip deflection versus beam impingement position for high frequency excitation of the cantilever of the instrument of FIG. 8.

A less intuitive characteristic of exciting a cantilever with a focused beam is that driving a cantilever to oscillate at its second and higher resonance modes produces a number of deflection peaks that increases with the order of the resonance mode. Hence, referring to the curves 354 and 356 of FIG. 10B, when the cantilever described in the preceding paragraph is excited to oscillate at its third resonance mode (58 kHz in the illustrated embodiment), three distinct deflection peaks are produced along the length of the cantilever. These peaks are denoted by points 358, 360, and 362, in the curve 356. Phase versus position along the cantilever is graphed by the curve 364 in FIG. 10B. Hence, cantilever deflection can be maximized or nearly maximized (hence maximizing cantilever response) by directing a beam at any of a number of different regions of the cantilever.

One important use of this capability is for surface elasticity characterization. Since the location of the nodes in these mode shapes are very sensitive to the surface properties at the tip-sample contact, the actuator can be positioned at a specific location relative to the cantilever free end and driven at a specific modulation frequency at which either the amplitude or phase of the mode shape changes very rapidly.

Figure 11:
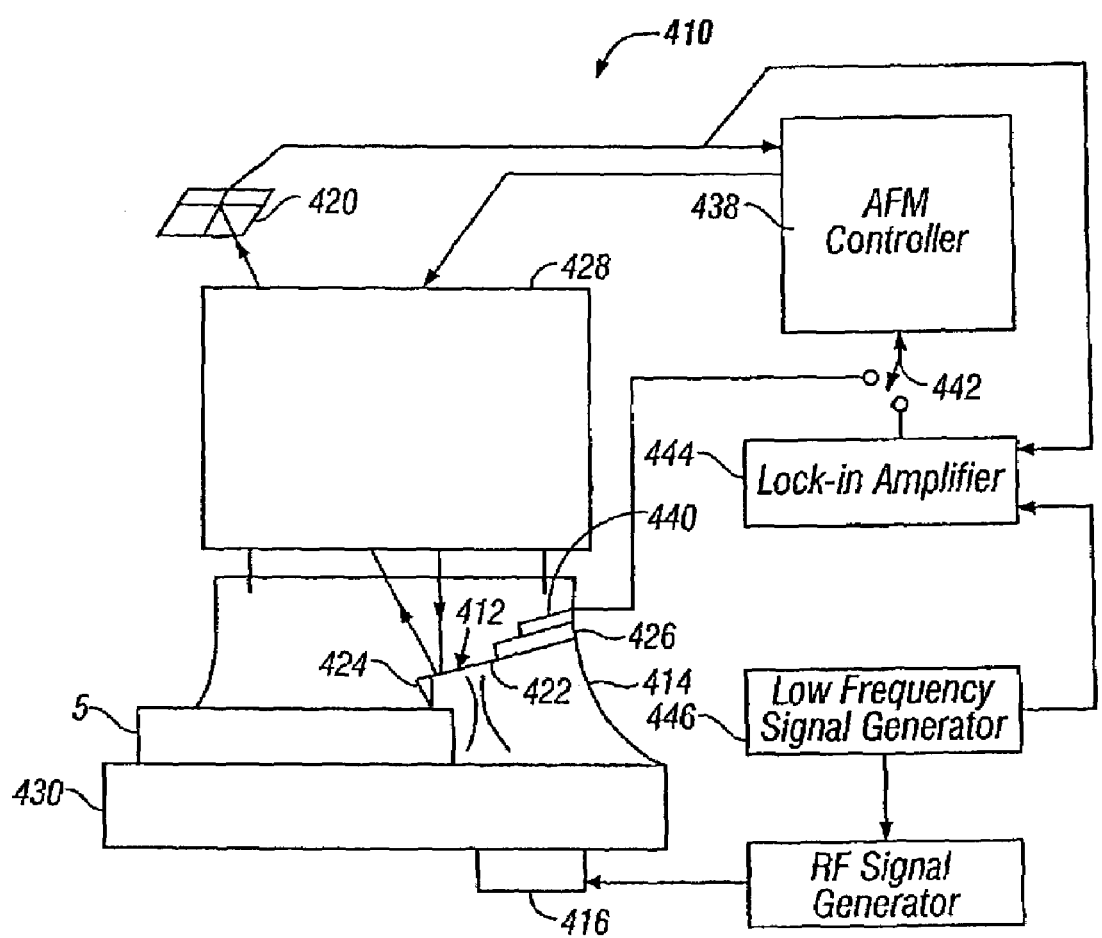
FIG. 11 schematically illustrates an ultrasonically actuated AFM constructed in accordance with a fourth embodiment of the invention in which the AFM is configured to take elasticity measurements.

An instrument 410 configured for elasticity characterization is illustrated in FIG. 11. It includes all of the components of the AFM of FIG. 8, including probe 412, a fluid cell 414, an ultrasonic transducer 416, a scanhead 428, a substrate 430, and a piezoelectric drive 440. The probe 412 includes a cantilever 422 that has a base mounted on a support 426 and that has a free end bearing a tip 424. Electronic components of the instrument 410 include an RF signal generator 432, an AFM controller 438, and a switch 442 selectively coupling the controller 438 to the RF signal generator and the piezoelectric drive 440. They additionally include a lock-in amplifier 444 and a low frequency signal generator 446. The lock-in amplifier 444 receives a feedback signal from the low frequency signal generator 446 and transmits an elasticity image signal to the AFM controller 438. Using conventional feedback to keep the force applied to the sample S constant, an image can be formed by monitoring cantilever deflection at the modulation frequency. The image, taking the form of an AC signal, has an amplitude and phase that both vary as a function of the sample stiffness. The procedure therefore can yield two simultaneous images: one for topography and one for surface elasticity. Elasticity characterizations using this technique can be performed much more rapidly than with prior known techniques due to the fact that the ultrasonic actuator has a dramatically higher bandwidth than prior systems that relied on a piezoelectric actuator to drive the entire probe up and down to obtain the required measurements. The prior systems typically had a maximum modulation frequency of only a few tens of kHz, whereas (as discussed above) an ultrasonic actuator based system has a cantilever actuation bandwidth of several MHz.

Figure 12A:
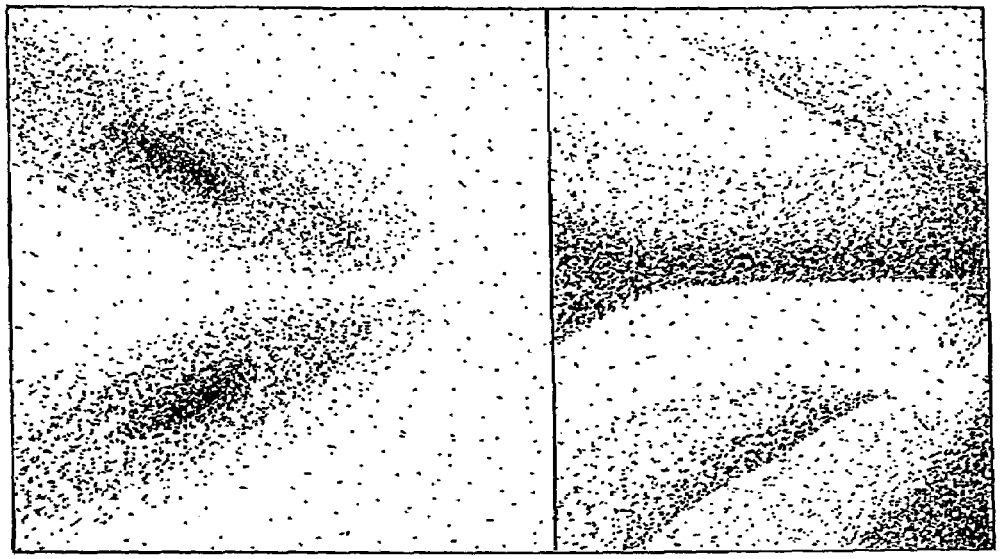
FIG. 12A is a comparative array of amplitude and phase images obtained by operating the AFM of FIG. 11 in a first torsional mode.
Figure 12B:
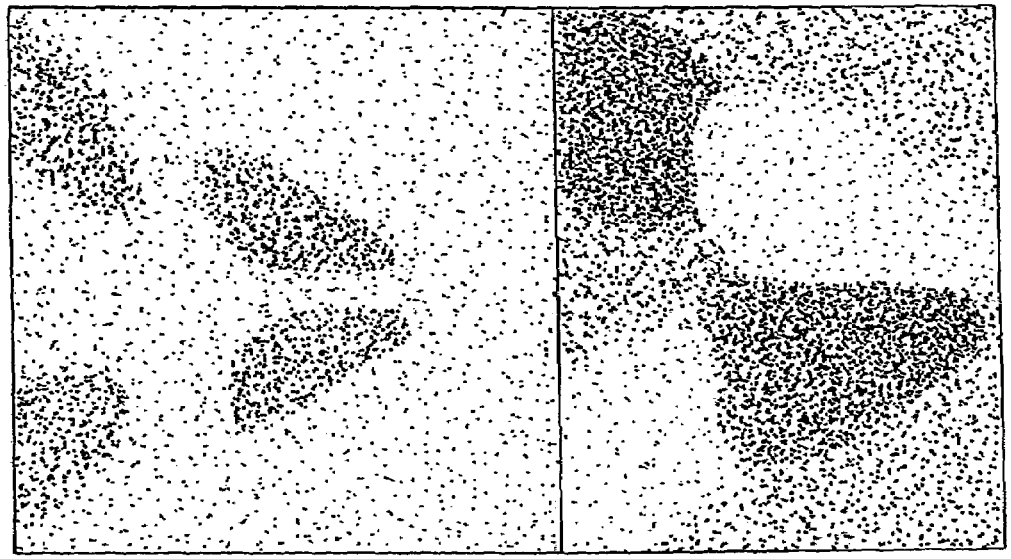
FIG. 12B is a comparative array of amplitude and phase images obtained by operating the AFM of FIG. 11 in a second torsional mode.

The same technique can be used to excite and measure the cantilever in torsional modes. For instance, FIGS. 12a and 12b show the amplitude and phase of the first two torsional modes of a V-shaped silicon nitride AFM cantilever.

G. No Focus Embodiment

Figure 13:
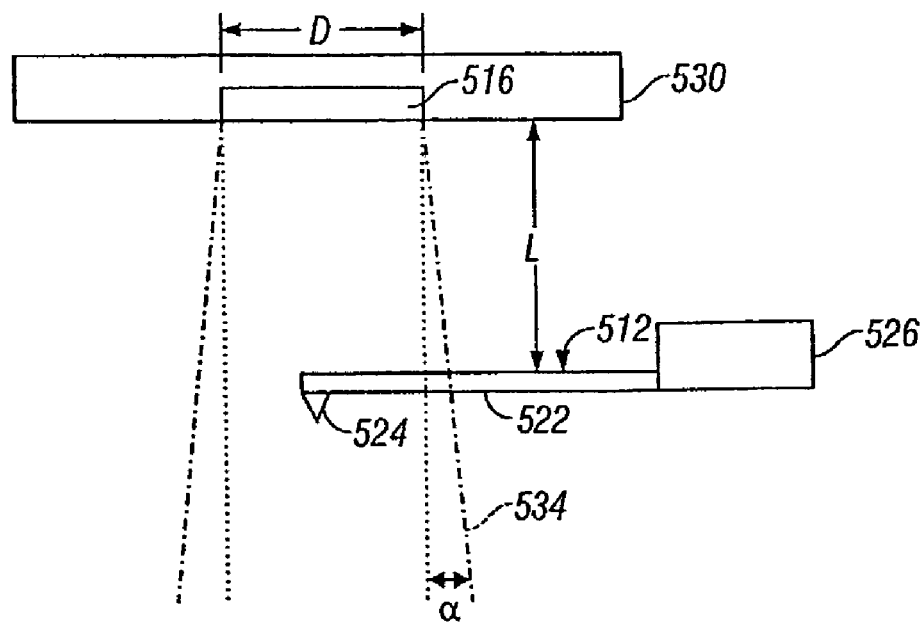
FIG. 13 schematically illustrates an ultrasonically actuated AFM constructed in accordance with another embodiment of the invention in which the ultrasonic actuator and related components are configured to transmit a collimated or minimally divergent beam onto the cantilever as opposed to a focused beam.

A focusing device is not required at all if the ultrasonic actuator is configured to produce a beam that is collimated, minimally divergent, or otherwise configured to impinge on the cantilever with sufficient precision to negate the need for a focusing device. An ultrasonic actuator 516 configured to produce a collimated beam is illustrated in FIG. 13. The actuator 516, which is mounted on a transparent holder 530, is configured to produce a slowly diverging beam 534, and the cantilever 522 is positioned with its body and free end in the beam 534 and the base and support 526 outside of the beam.

Beam divergence can be minimized using well-known ultrasonic transducer design techniques such as are disclosed, for example, in G. S. Kino "Acoustic Waves, devices, imaging and analog signal processing" Prentice-Hall, 1987, Englewood Cliffs, N.J. In general, the requirements for minimum beam divergence can be derived from diffraction calculations. One way of optimizing the energy collimation would be to place the probe at a distance where the near-field to far-field transition happens. For a circular actuator with diameter D, this distance is given by $L=D^2/\lambda$, where D is the diameter of the actuator and $\lambda$ is the wavelength of the ultrasonic waves in the medium ($\lambda$=speed of sound/frequency). For a rectangular actuator which is very long in one dimension (as shown in FIG. 9) and has of width W, the optimum distance will be $L\sim W^2/4\lambda$. At this distance, the ultrasonic energy will be dominantly on the axis. For smaller distances, in the near-field, the ultrasonic energy will rapidly fluctuate, and the exact position of the probe will be more critical.

For distances larger than $L=D^2/\lambda$ ($W^2/4\lambda$), the beam will diverge with a divergence angle of $a=\mathrm{asin}(1.22\,\lambda/D)$ for a circular actuator and $a=\mathrm{asin}(\lambda/W)$ for a rectangular transducer. Therefore, one way (but by no means the only way) of limiting beam divergence is by maximizing the frequency f of the beam 534 and minimizing the diameter D at the base of the beam as determined by the diameter of the ultrasonic actuator 516. Because f is inversely proportional to the wavelength ($\lambda$) of the ultrasonic signal, the divergence (a) can be kept very small by minimizing both D and $\lambda$ within practical limits. (As discussed above, this may not be the case for near field applications) A divergence of less than 10 degrees is preferred, but an effective actuator could still be designed with a divergence of 30 degrees or more. This effect can be achieved by placing a small ZnO actuator having a mean width on the order of 50–500 microns directly above the cantilever at a spacing of L up to several mm without any focusing. The actuator can be made in a variety of shapes—circles, ovals, rectangles or other arbitrary shape to provide the desired ultrasonic beam profile.

Using either focusing or collimation, the beam may be made intentionally smaller than the cantilever so that all of the energy strikes the cantilever. This embodiment is preferred for applications where the ultrasonic actuator is used to apply a very well known force to the cantilever, for example to measure the spring constant of a cantilever or to apply a known force from the cantilever to the sample. In an alternate embodiment, the beam may be intentionally sized larger than the cantilever to account for tolerances in the alignment of the cantilever and the ultrasonic actuator. If for example, the cantilever is 50 microns wide and can be reproducibly aligned within ±100 microns, an ultrasonic actuator with a beam width of 250–300 um in the region of the cantilever could guarantee that a portion of the ultrasonic beam would always strike the cantilever. In the preferred embodiment, actuator sizes range from minimum widths of about 50 um up to about 3 mm.

H. AFM Array with Integrated ARP Actuation

Figure 14A:
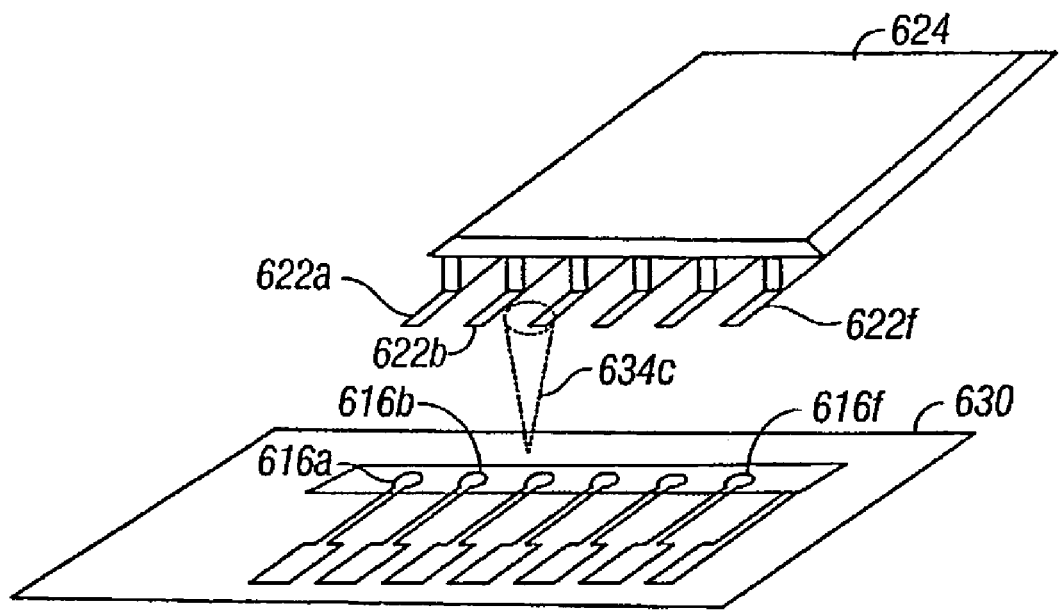
FIG. 14A schematically illustrates a portion of an ultrasonically actuated cantilever array showing an array of ultrasonic actuators matched to an array of cantilevers.

The ARP method can be easily used to actuate AFM cantilevers in an array. FIG. 14A shows the schematic of one of these cantilever arrays. A plurality of ultrasonic actuators 616a, 616b, etc., are mounted on a common transparent holder 630. Each actuator is configured to direct a beam (beam 634d for example) of ultrasonic energy at a corresponding cantilever 622a, 622b, etc. of an array of cantilevers mounted on a common support 624. As with the previous embodiments, the actuators can be accompanied by focusing lenses, collimation or other beam confinement, phase array as necessary.

Figure 14B:
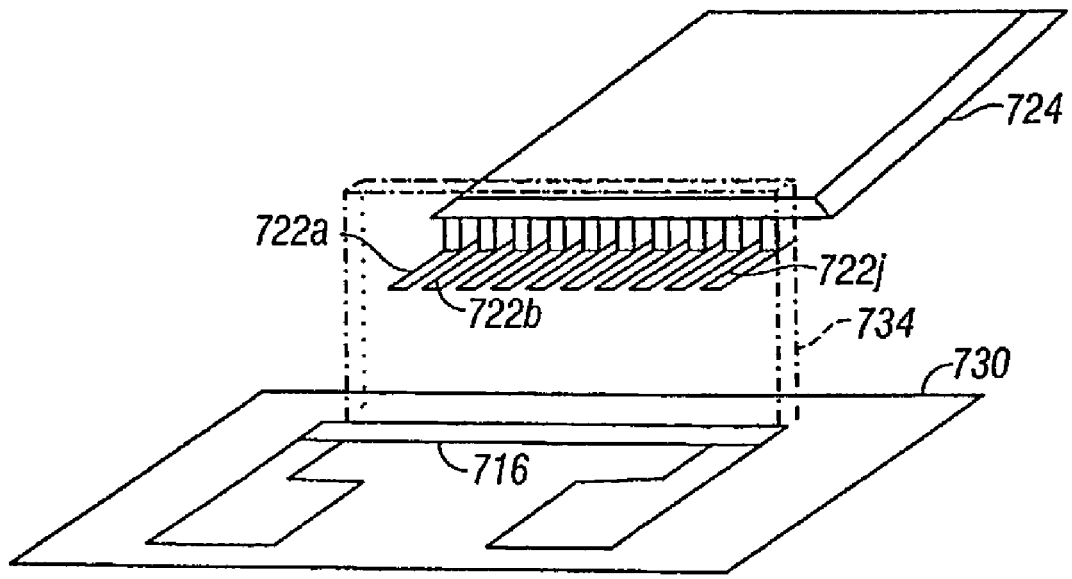
FIG. 14B schematically illustrates a portion of an ultrasonically actuated cantilever array with a single rectangular ultrasonic actuator arranged to excite the array of cantilevers.

In an alternate embodiment shown in FIG. 14B a single rectangular aperture can be provided in a holder 730 and configured to transmit a wide ultrasonic beam 734 from a single ultrasonic actuator 716 that strikes all the cantilevers 722a, 722b, etc. of the array at once. The divergence of the beam 734 can be reduced as necessary using a lens or using the techniques described above in conjunction with the "No Focus" embodiment of FIG. 13. Cantilever arrays for AC applications are usually designed to have different resonant frequencies so that the oscillation of one cantilever does not excite a sympathetic vibration of adjacent cantilevers. With this type of array, the modulation frequency can be tuned to oscillate one cantilever at a time so that the dynamic properties of the individual cantilevers in the array can be measured. The rectangular actuator arrangement 716 of FIG. 14B requires higher power to energize the larger actuator, but it has the advantage of not requiring a switching circuit to energize the actuators individually as in FIG. 14A.

II. Electromagnetic Drive

The ultrasonic drive discussed above operates very well on liquids. However, it does not operate well in a gas such as air because an ultrasonic actuator requires an acoustic impedance match between the ultrasonic actuator and the medium. When there is an acoustic impedance mismatch between the actuator and the medium, as is the case when a cantilever is driven in a gas, the ultrasound beam is reflected at the interface between the gaseous media and actuation elements and is unable to reach the cantilever. Another drawback of an ultrasonic drive is related to an acoustic streaming force generated by the ultrasound beam in fluid. This force is generated by the attenuation of the ultrasonic energy in the fluid which causes momentum transfer from the wave to the fluid itself. This relatively large pressure gradient in fluid will induce convection flow of the fluid, impacting the cantilever by turbulence and uncontrollable random local pressure fluctuations. This gradient produces so-called "acoustic streaming noises" that lead to the imposition of spurious and transit forces on the cantilever. The resulting cantilever deflection can be difficult to distinguish from deflection resulting from forces generated directly by the acoustic actuator. In addition, because the acoustic streaming noise-generated forces are spurious and uneven, the effective central point of forces imposed by the ultrasonic beam on the cantilever can move both laterally and longitudinally along the cantilever, causing the cantilever to twist and also varying the moment arm on the cantilever.

An electromagnetic drive does not experience these problems because it does not require acoustic impedance matching between the drive and the medium in which the cantilever is immersed. It therefore can be used in both liquid and gaseous media. Some basic aspects of its theory of operation and several embodiments will now be described.

A. Theory of Operation

As indicated above, an electromagnetic drive imposes a force on a cantilever by transmitting an AC signal through an electromagnetic actuator spaced from but preferably located in the vicinity of the cantilever. The AC signal preferably is a radio frequency (RF) signal formed at least in part from a high frequency carrier signal having a frequency that is substantially higher than the resonant frequency of the cantilever. The resulting electromagnetic wave interacts with a cantilever to impose a bending force on the cantilever. The high frequency carrier signal may, if desired, be modulated with a lower frequency modulation signal to induce the cantilever to oscillate, preferably at resonance. Cantilever response can then be monitored either directly in response to the imposition of electromagnetic interaction and/or in response to probe/sample interaction to obtain measurements regarding characteristics of the sample, the environment, and/or the cantilever. The force, or at least an interactive component of it, is believed to result from an induced electromagnetic (IEM) interaction between the electrically conductive cantilever and the electromagnetic actuator upon actuator energization. Bending forces may also be imposed on the cantilever by the induction of thermal stress gradient in the cantilever as a result of the energization of the electromagnetic actuator. The electromagnetic drive has most or all the benefits of the ultrasonic actuator described above and has the additional benefit of being able to effectively operate in both gases and liquids, whereas an ultrasonic actuator only operates effectively in liquid.

Figure 15:
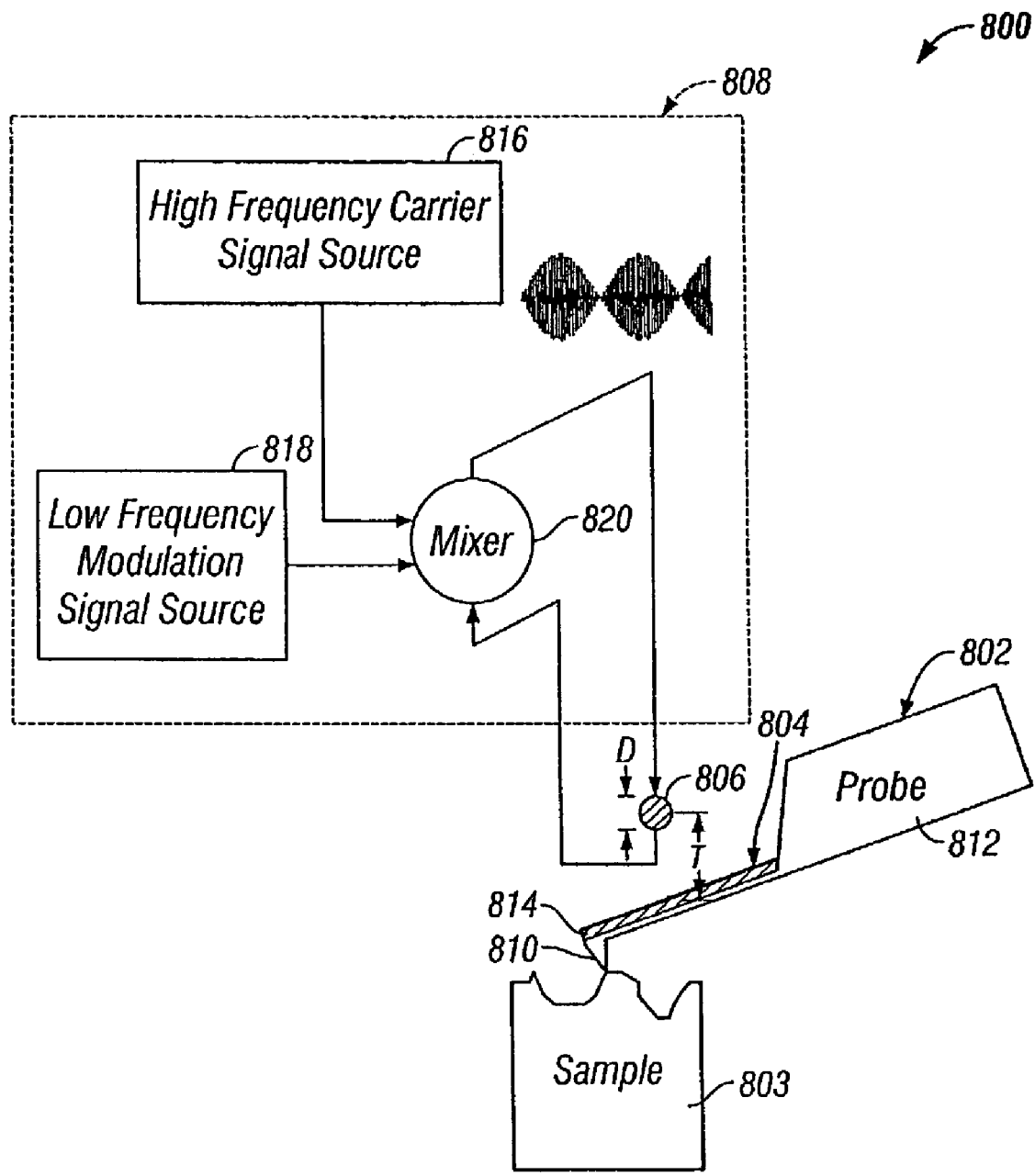
FIG. 15 schematically illustrates a probe driven by an electromagnetic drive constructed in accordance with another preferred embodiment of the invention.

Turning now to FIG. 15, an electromagnetic drive 800 and the associated electrically conductive probe-based cantilever 802 are illustrated. The probe 802 includes a cantilever 804 at least a portion of which is electrically conductive. The electromagnetic drive 800 comprises an electromagnetic actuator 806 located in the vicinity of the cantilever 804 and a signal source or drive circuit 808 that supplies an AC signal to the actuator 806 so as to impose the above-described interactive force on the cantilever 804.

Except for having an electrically conductive cantilever 804, the probe 802 is conventional and may be any type commonly used with probe-based instruments. For instance, it could be part of a cantilever array. In the illustrated example, the cantilever 804 is a simple micro-cantilever having a tip 810 mounted or otherwise provided on a free end of it. The base of the cantilever 804 is fixed to or formed integrally with a probe support 812, which may fit into a commercial AFM scanhead. The cantilever 804 of this example, like that described above in connection with the ultrasonic actuator, is made of silicon. Cantilevers of this type typically have a length of 10 micron to 400 microns, a width of 5 microns to 40 microns, and thickness of 0.2 micron to 5 microns. An exemplary cantilever having these characteristics has a length of about 100 μm, a width of about 40 um, and a thickness of about 700 nm. It has a spring constant of 0.148 N/m and a fundamental resonance around 4.6 kHz in water and 15 kHz in air.

To the extent that IEM interactive forces are generated, at least a portion of the cantilever 804 must be electrically conductive in order to interact with the electromagnetic actuator 806. (However, thermal and/or electrostrictive stresses may be induced in the cantilever even if the cantilever is not electrically conductive. Electrostrictive stresses can be employed, e.g., to drive the cantilever to deform and oscillate at or below the resonant frequency thereof.) The term "at least a portion" as used herein should be understood to mean a sufficient percentage of the cantilever's surface area to induce a electromagnetic field when the actuator 806 is energized. The entire surface of the cantilever facing the actuator 806 (and possibly part or all other surfaces of the cantilever body as well) may be rendered conductive for this purpose. Alternatively, if only a portion of the cantilever is rendered conductive, that portion should preferably be located away from the base of the cantilever. As with the ultrasonic actuator described above, that portion should be even more preferably located as close as practical to the cantilever free end so as to maximize cantilever deflection for a given IEM field strength without interfering with cantilever motion detection. Various techniques may be employed to render the cantilever electrically conductive. Some of these techniques are better suited for some applications than others.

For example, the cantilever may be rendered electrically conductive by coating all or a portion of the surface facing the actuator 806 (the upper surface in this embodiment) with a thin layer 814 of an electrically conductive material such as Al, Au, or another conductive material or materials. The layer 814 can be deposited on the cantilever, for example, by evaporation or chemical deposition. The conductive layer 814 need only be thick enough to provide the required electrical conductivity and may be as thick as desired so long as it does not significantly interfere with cantilever stiffness. Coating thicknesses of 10–50 nm are typical.

Likewise, the deformation of the cantilever can also be induced by a thermal gradient caused by RF radiation. In this case, a non-conductive cantilever may also be excited to oscillate mechanically.

The electromagnetic actuator 806 may comprise any of a variety of devices that imposes a force on the cantilever 804 when it receives an AC signal from the drive circuit 808. The actuator 806 of this embodiment comprises a "micro wire," i.e., a thin wire. The micro wire of the illustrated embodiment comprises a cylindrical rod that extends at least generally transversely relative to the cantilever 804. It can be located either above or below the cantilever 804 so long as its placement does not interfere with cantilever mounting, sample placement, or cantilever motion detection. The wire has a diameter "D" and a length "L" (see FIG. 16). It is spaced from the cantilever 804 by a gap having a thickness "T". The diameter "D" of the wire may vary significantly depending on the application and designer preference. It is preferably as small as practical so as to maximize the current density induced by the flow of the drive current through the wire. Diameters of 10–200 microns or possibly even larger are feasible, with a diameter of 10–50 microns being preferred and 10–25 microns being especially preferred. The length "L" of the wire should at least be on the order of the width of the cantilever. As discussed above, this width typically is 30 µm. The thickness "T" of the gap should be small as practical so as to maximize the strength of the induced field without interfering with the cantilever mounting, cantilever movement, or cantilever motion sensing. Spacings of less than 10 microns to more than 200 microns are feasible. A spacing of about 50 microns is currently preferred.

The signal source or drive circuit 808 may comprise any circuit that could be selectively actuated to deliver an AC signal to the electromagnetic actuator 806 that results in the imposition of a force on the cantilever 804. It is also desirable in many systems that drive circuit 808 additionally be capable of periodically modulating the amplitude of the high frequency carrier signal so as to cyclically vary the effective signal strength being delivered to the electromagnetic actuator 806. The drive circuit 808 of the embodiment of FIG. 15 performs these functions using a high frequency carrier signal source 816, a low frequency modulation signal source 818, and a mixer 820. The mixer 820 has first and second inputs connected to outputs of the carrier signal source 816 and the modulation signal source 818, respectively, and has an output connected to the electromagnetic actuator 806.

The carrier signal source 816 is configured to generate a high frequency carrier signal and to transmit that signal to the mixer 820. "High frequency" as used herein means that the carrier signal is substantially higher than the resonant frequency of the cantilever 804. The optimal carrier signal frequency for a given circuit will vary, e.g., with the length of the micro wire or other electromagnetic actuator employed and designer preference. Carrier frequencies will typically be between about 10 MHz to about 300 MHz, and will preferably between about 50 MHz and 250 MHz in most applications. These frequencies are typically in the range of 10 to 1000 times the resonant frequency of the cantilever and fixed around 150 Mhz in the preferred embodiment. An RF VCO (voltage control oscillator) is well suited to generate signals of this frequency range. A digital frequency synthesizer could also be employed.

The modulation signal source 818 is configured to generate a modulation frequency that, when mixed with the high frequency carrier signal in the mixer 820, modulates the carrier signal to produce an AC drive signal that the amplitude of the carrier signal varies cyclically so as to drive the cantilever to oscillate. The preferred modulation frequency for a particular application is dependent upon cantilever properties and designer preference. For exciting cantilever resonance, the best results are obtained if the modulation frequency is set to match the cantilever's fundamental resonant frequency or an overtone or half overtone of that frequency. The modulation frequency preferably is either the cantilever's fundamentally resonant frequency or one of the first five overtones thereof. The resulting frequency would typically be on the order of about 1 KHz to a few MHz in most applications. Other AC or even DC modulation signals could be generated.

The mixer 820 preferably comprises an unbalanced mixer that offsets the signal from modulation signal source 818 so that it is centered around a value of, e.g., half its amplitude rather than zero. It also multiplies the signal from the carrier signal source 816, hence generating a amplitude modulated waveform that is centered around the offset value.

Figure 16:
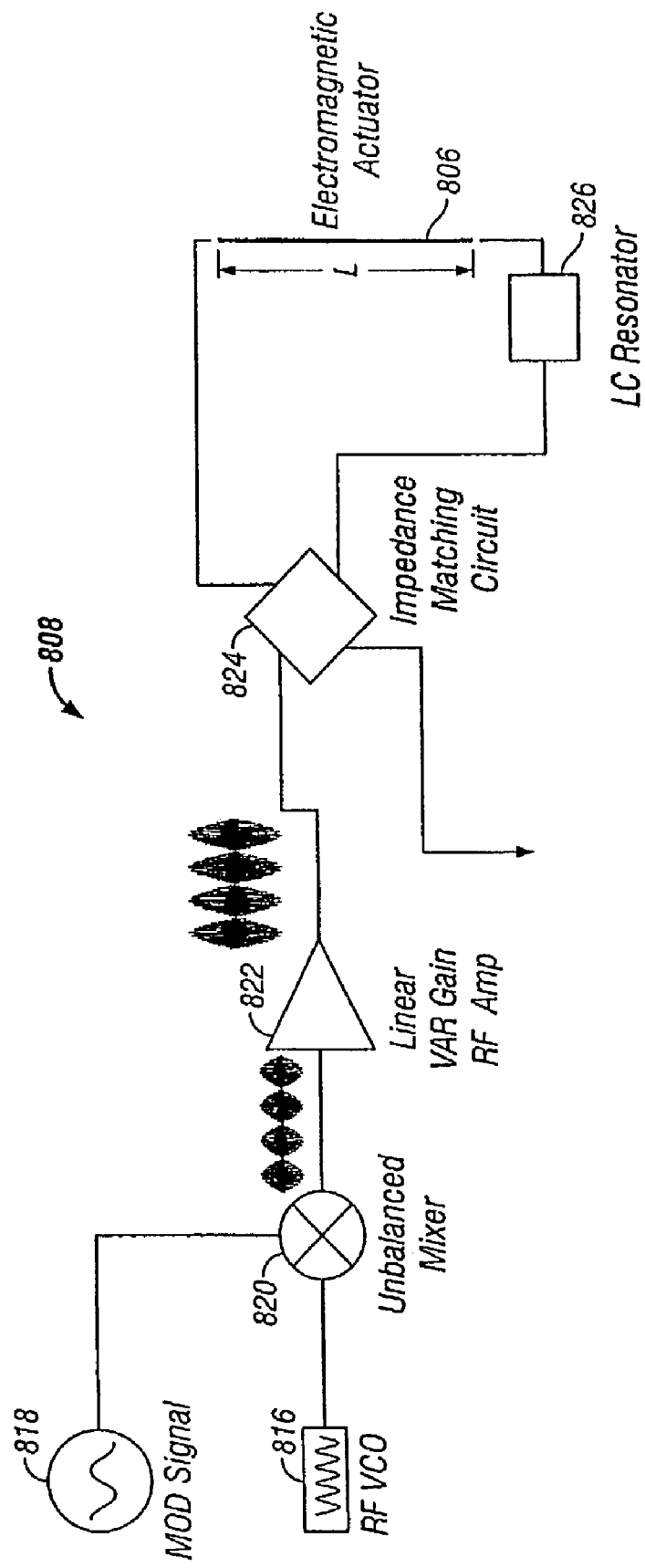
FIG. 16 is a circuit schematic illustrating additional details of a preferred drive circuit of the electromagnetic drive of FIG. 15.

Turning now to FIG. 16, a preferred embodiment of the drive circuit 808 illustrated in FIG. 15 is shown in greater detail. The circuit 808 comprises the high frequency carrier signal source 816, the low frequency modulation signal source 818, the mixer 820, a variable gain amplifier 822, an RF electrical impedance matching circuit 824, and an LC resonator 826. The carrier signal source 816, modulation signal source 818, and mixer 820 are described above.

The variable gain amplifier 822 amplifies the waveform from the mixer 820 by a multiplier that can be adjusted by manipulation of the amplifier, hence varying the amplitude of cantilever oscillation. This function can be performed by a single component or two or more interconnected components such as a fixed amplifier and a variable attenuator.

The impedance matching circuit 824 is employed to account for the fact that most RF components are designed for a 50 ohm circuit, whereas the electromagnetic actuator 806 is unlikely to have the same impedance. Circuit 824 matches the impedance of the signal from the amplifier 822 to the impedance of the actuator 806. A transformer may be suitable for this task.

It may worth to point out here that impedance matching is in reference to an RF electromagnetic signal and has the effect of enhancing drive efficiency. It is an entirely different concept as compared to acoustic impedance matching for ultrasonic signals. The latter is the matching of mechanical properties for ultrasound propagation, and much more difficult to accomplish.

Finally, the LC resonator 826, combined with the parasitic reactance due to the environment, determines the resonance of the electromagnetic actuator. Hence, it sets the frequency of the drive signal to one that maximizes the system's response. This frequency is dependent primarily on the length "L" of the actuator 806. It can be calibrated during system setup. The purpose of this local oscillator is to maximize the current that is delivered to the wire conductor/actuator 806.

The electromagnetic drive 800 as described above provides vastly improved response with higher bandwidth when compared to most other piezo, electrostatic or magnetic static drives and, unlike the ultrasonic drive discussed in Section I above, does not require acoustic impedance matching with the environment and, therefore, can be used in gas or ambient.

Figure 17A:
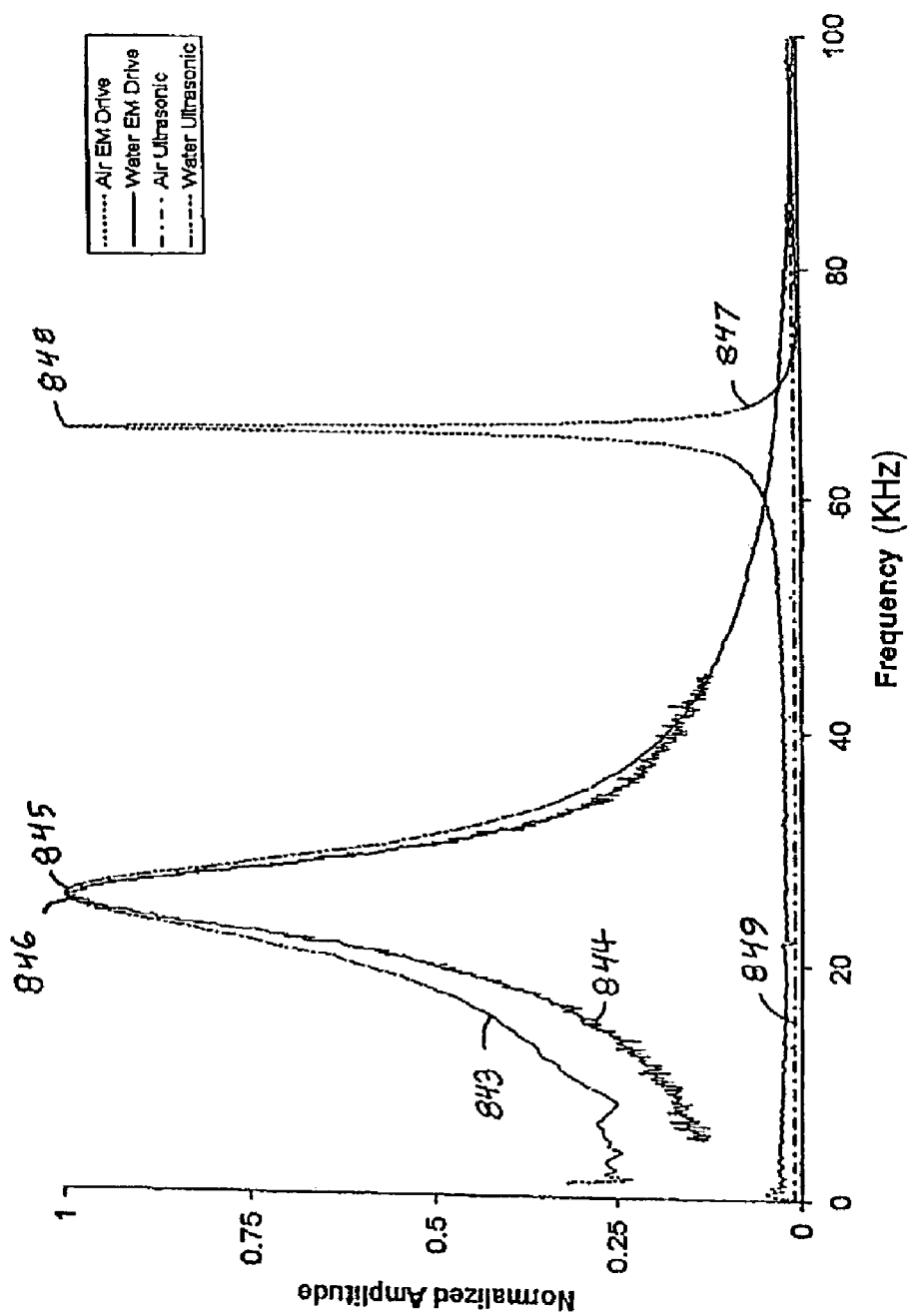
Figure 18:
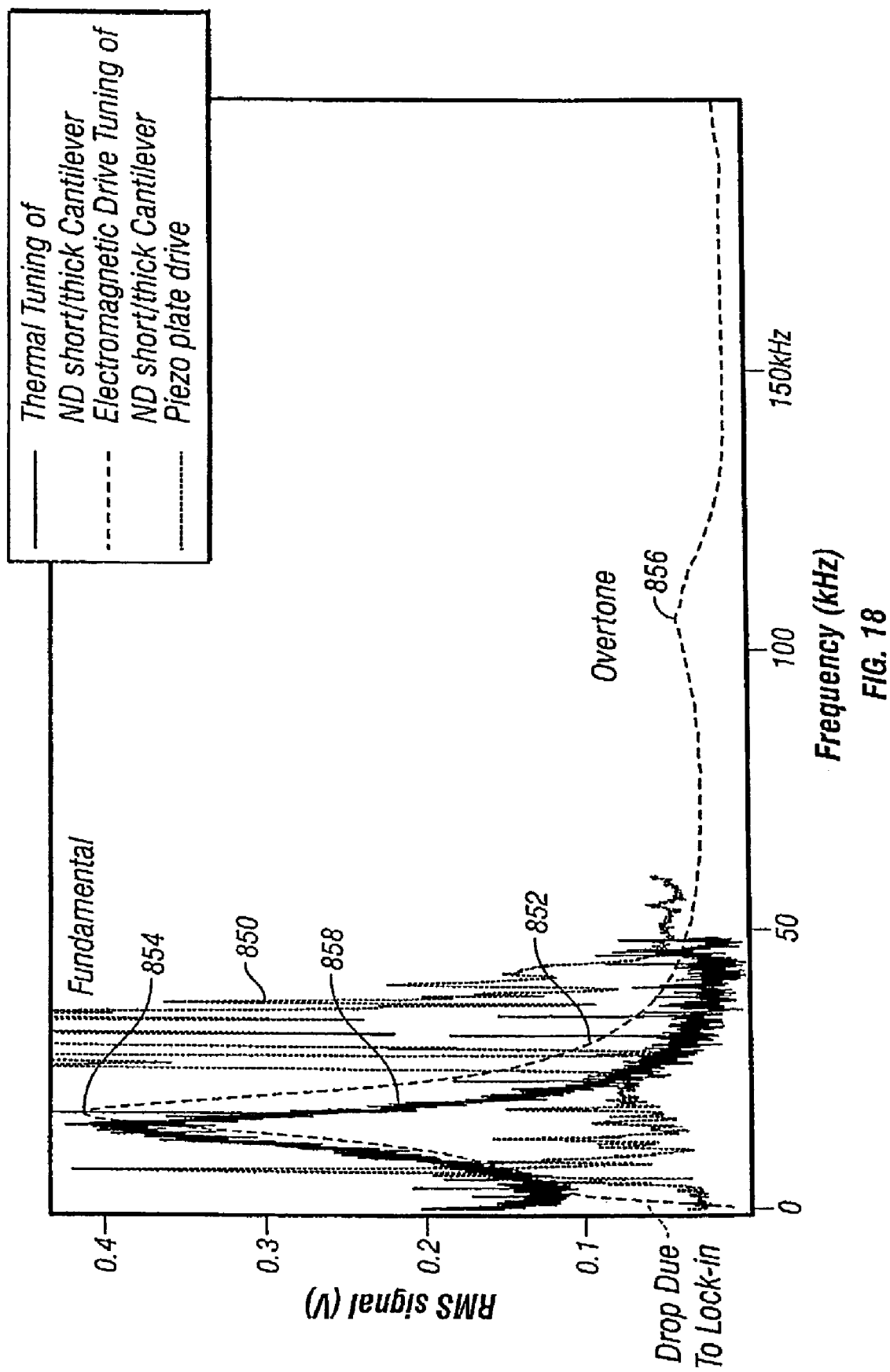

These characteristics are illustrated graphically in FIGS. 17, 17A, and 18. FIG. 17 generally corresponds to FIG. 7A above to the extent that it plots RMS deflection vs. drive frequency for a relatively short, thick cantilever (having a length of about 100 μm and a thickness of about 700 nm) as it is driven by various drives. This figure illustrates the similar performance of electromagnetic drive in comparison with the ultrasonic drive (FIG. 7a) when the cantilever oscillates in water. Curve 830 plots the cantilever's response to excitation via an acoustic drive of the type illustrated in FIG. 1C, curves 832 and 834 plot the response to a traditional voice coil drive with the tip holder clamped to its support and unclamped from its support, respectively, and curve 836 plots the response to an electromagnetic drive constructed in accordance with the invention. The true response of the cantilever, as determined via thermal tuning, is reflected by the curve 838. Point 840 of curve 838 indicates that the cantilever actually experiences a fundamental resonance at about 15 kHz. Curves 830, 832, and 834 indicate that it is virtually impossible to differentiate cantilever resonance from other parasitic resonances when the cantilever is driven by a conventional acoustic drive or a voice coil drive. In sharp contrast, the cantilever resonance as excited by an electromagnetic drive can be clearly detected at point 842 in curve 836. This effect is believed to be due at least in part to the fact that the actuator acts at least primarily on the cantilever. The mechanical energy output for the actuation part is in the same order of magnitude as the dynamic energy of the cantilever oscillation. This is in sharp contrast to a piezo plate or voice coil drive, where the mechanical energy of the actuation part is usually $10^4$ to $10^5$ times more than cantilever dynamic energy. The surplus energy is responsible for parasitic resonances in the prior art drives rather than other components of the system and, accordingly, induces far fewer and smaller-amplitude parasitic resonances.

FIG. 17A compares the response of a micro-cantilever as it is driven in both air and water by both an ultrasonic actuator constructed in accordance with the first embodiment of the invention and an electromagnetic actuator constructed in accordance with the embodiment. Curves 843 and 844 confirm that the response to both drives is excellent when the cantilever is oscillated in water, with cantilever resonance being easily detected at points 845 and 846 in the respective curves 843 and 844. The peak 848 at resonance on the curve 847 also reconfirms that the response of the same cantilever in air is excellent when the cantilever is driven by an electromagnetic drive. However, curve 849 demonstrates that, when the cantilever operating in air, the mismatched impedance prevents ultrasonic beam from reaching the cantilever and therefore no resonance is detected.

FIG. 18 plots the response of the same type of cantilever over a larger frequency range while the cantilever, immersed in water, is excited by a traditional piezo drive and an electromagnetic actuator, respectively. Curve 850 demonstrates that the piezo drive exhibits essentially the same limitations as the acoustic drive. Curve 852, which plots the response of the same cantilever to excitation by an electromagnetic drive, is tantamount to an extended version of the curve 836 of FIG. 17. The peaks 854 and 856 on curve 852 illustrate that both the fundamental resonant frequency and overtones can also be detected when the cantilever is excited by an electromagnetic drive. Curve 858 once again confirms that this response accurately reflects the pure cantilever response as determined by thermal tuning.

Unlike an electrostatic drive force, which scales down with a reduction in the area of the interaction, reducing the area of interaction of an electromagnetic drive, e.g., by producing thinner and smaller diameter electromagnetic actuator 806 when compared to the wire in FIG. 15 provides a stronger drive while other conditions are kept identical. Shorting the conductive surface of the cantilever to ground the end of the drive wire element does not change the drive efficiency. These observations indicate that the interaction force is not an electrostatic force. Furthermore when the RF signal produced by the carrier signal source 816 is reduced to zero, the low frequency signal produced by the signal source 818 is incapable of driving the cantilever under all circumstances. The RF (carrier) component of the signal therefore appears to be important to the production of the interactive force that deforms the cantilever. Its interaction also includes an induced eddy current in the cantilever and local gradient heating on the cantilever by the RF signal. In the latter case, the thermal gradient would induce thermal stress in the cantilever which, in turn, imposes forces on the cantilever that deforms it in the absence of countervailing forces.

B. Practical Examples

Practical examples of the generic system described in Section IIA above will now be described. These examples, like the more generic examples set forth above, are provided only for explanatory purposes and are nonlimiting.

1. AFM Application

Figure 19:
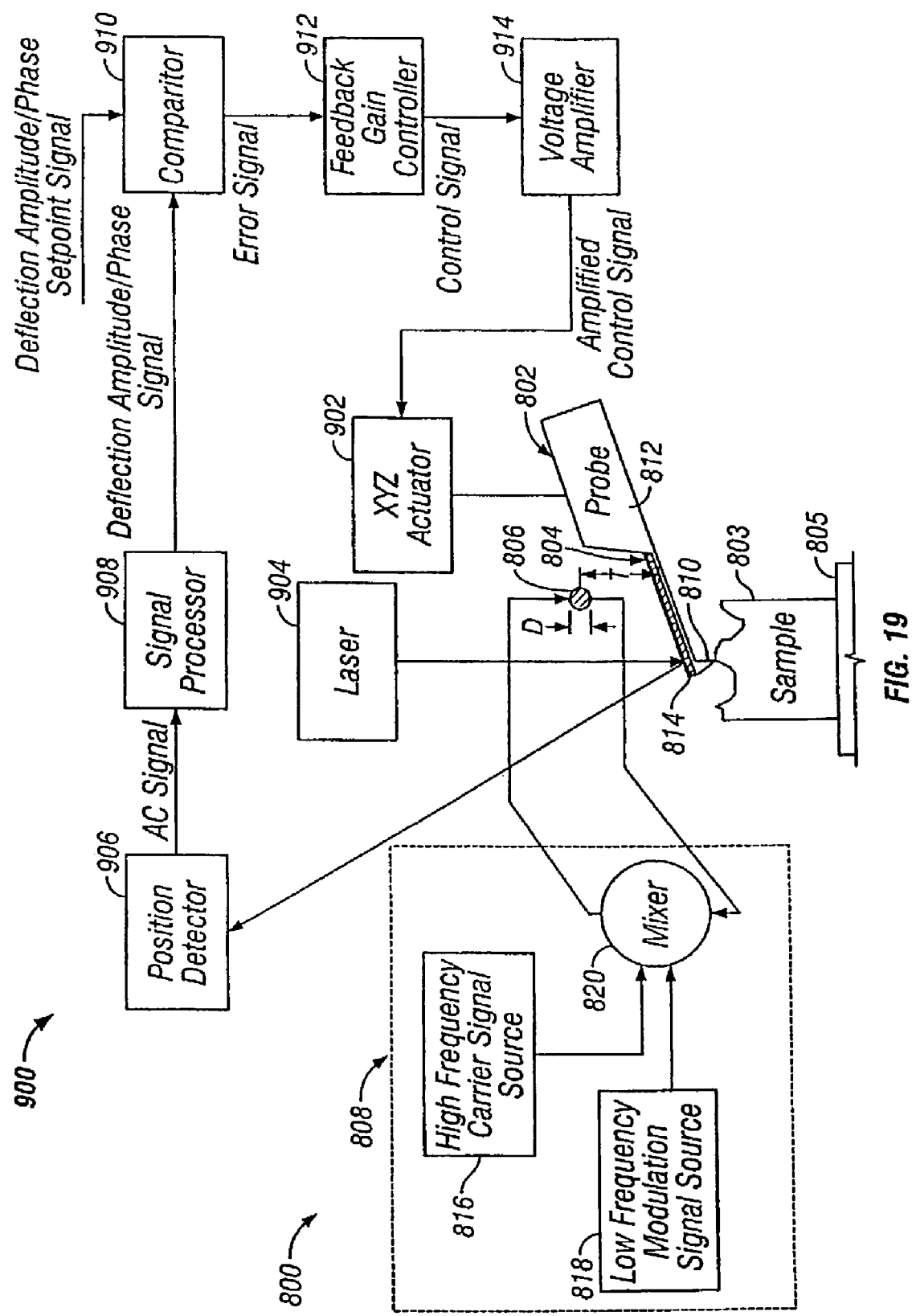
FIG. 19 schematically illustrates an atomic force microscope (AFM) fitted with an electromagnetic drive of the type generally illustrated in FIG. 15.

Referring now to FIG. 19, an atomic force microscope (AFM) 900 is schematically illustrated that incorporates the cantilever drive system 800 described above. As described above in connection with FIG. 15, that drive includes an electromagnetic actuator 806 such as a micro wire and a signal source or drive circuit 808 including a high frequency carrier signal source 816, a low frequency modulation signal source 818, and a mixer 820. The drive 800 imposes a force on an electrically conductive cantilever 804 of a probe 802 upon energization of the actuator 806 with an amplitude modulated RF wave. The additional drive circuit components of FIG. 16 are also included but omitted from this discussion for the sake of conciseness. As is typical of AFMs, an actuator (the electromagnetic actuator 806 in this case) is controlled to drive the cantilever 804 to operate at or near its resonant frequency. As is also typical of AFMs, the cantilever 804 of this embodiment bears a probe tip 810 configured to interact with a sample 803 positioned on sample support 805 located beneath the probe 802. The probe base 812 is connected to a translational actuator such as an XYZ actuator 902 that selectively drives the probe 802 in a horizontal (XY) plane to effect a scan such as a raster scan and in a vertical (Z) direction to obtain measurements such as surface topography measurements. Of course, a portion or all of the actuator 902 could be connected to the sample support 805 to translate the sample 803 rather than the probe 802.

The AFM 900 additionally includes components that detect cantilever motion, compare one or more characteristics of that motion to corresponding setpoint(s), and adjust AFM operation, usually the Z position of the cantilever 804 relative to sample 803 through XYZ actuator 902, and obtains measurements based on the response of the AFM's actuator(s) in order to maintain cantilever deflection amplitude or another parameter of cantilever oscillation at a constant, or setpoint. A variety of different systems and subassemblies are available for this purpose. In the illustrated exemplary embodiment, cantilever motion is detected using an optical lever system that is identical to that of the AFM of FIG. 11. The detector therefore includes a laser 904 positioned above the cantilever 804 and a four-quadrant photodetector 906 configured to receive laser light reflected from the upper surface of the cantilever 804. A signal processor 908 receives the AC signal from the detector 906 which is outputs AC signal(s) indicative of one or more characteristics of cantilever oscillation, such as phase or rms of oscillation amplitude. Each resulting value is compared with a corresponding setpoint value in a comparator 910 to obtain an error signal. The resulting error signal is then transmitted through a feedback circuit such as a gain controller 912 to produce a control signal. The control signal is amplified in a voltage amplifier 914 to produce an amplified control signal. The comparator 910, feedback gain controller 912, voltage amplifier 914, and possibly the signal processor 908 may be contained within a single computer of the type commonly employed in AFMs. The amplified control signal is transmitted to the XYZ actuator 902 to move the probe 802 in the Z direction to maintain the monitored parameter at the setpoint(s) as the probe 802 is driven to scan in the XY plane. The same signal also serves as a measurement of sample surface topography or another sample characteristic, which then can be displayed via any suitable device in a conventional manner.

All of these functions are standard in an AFM operating in fluid, but the resulting measurements can be obtained with enhanced accuracy with a vastly increased bandwidth than corresponding measurements using a cantilever actuated in a conventional manner. They can also be obtained while the probe operates in air or another gaseous medium—a function that is not easily implementable with an ultrasonically actuated cantilever.

2. Environment/Probe Characteristic Detector

Figure 20:
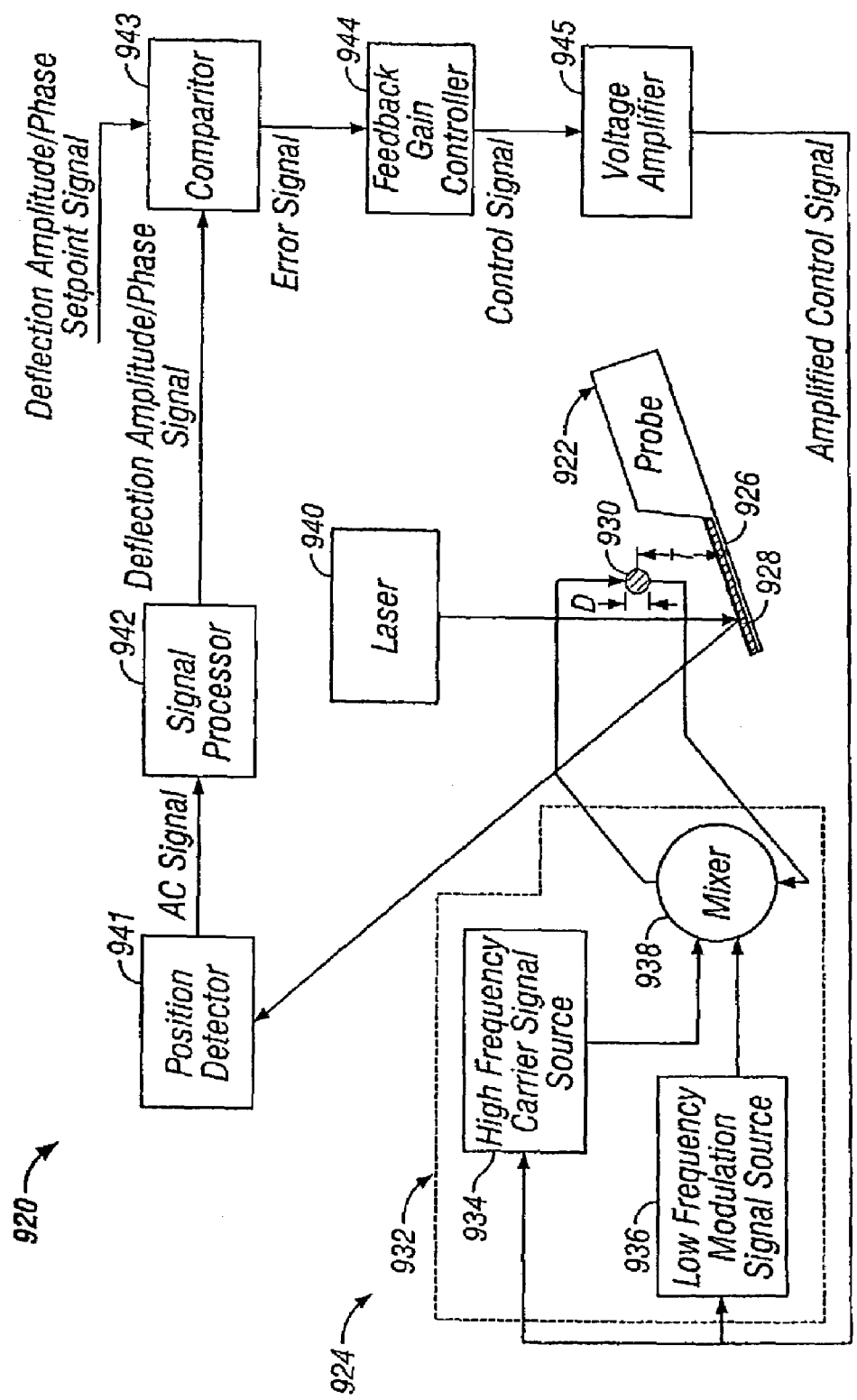
FIG. 20 schematically illustrates another probe-based instrument fitted with an electromagnetic drive of the type generally illustrated in FIG. 15.

An electromagnetic drive can also be used in a nontraditional AFM environment to obtain information regarding the environment or the probe itself. The probe of this type of instrument does not interact with a sample using tips. It instead uses the feedback signal from a comparator to adjust the high frequency carrier source and/or low frequency modulation source. A probe-based instrument 920 of this type is schematically illustrated in FIG. 20. The instrument 920 includes a cantilever-bearing probe 922 and an electromagnetic drive 924 configured to operate generally as described above. Hence, the probe's cantilever 926 is coated with a layer 928 of a conductive material or is otherwise rendered electrically conductive. However, because the probe 922 of this embodiment does not interact with a sample, the cantilever 926 need not have a tip. The cantilever 926 is excited by an electromagnetic actuator 930 such as a micro wire. The actuator 930, in turn, is energized by a drive circuit 932. The drive circuit 932 includes a high frequency carrier signal source 934, a low frequency modulation signal source 936, and a mixer 938. Other components of the drive circuit 932, described above in connection with the drive circuit 808 in FIG. 16, are omitted from FIG. 20 for the sake of conciseness.

The instrument also includes a laser 940, a position detector 941, a signal processor 942 which yields phase and rms of the deflection signal, a comparator 943 to produce error, a feedback gain controller (or phase shifter in case the setpoint is a phase value) 944, and a voltage amplifier 945, all of which operate as described above in connection with the AFM embodiment of FIG. 19. However, rather than transmitting its output to an XYZ actuator, the voltage amplifier 945 transmits its outputs to the high frequency carrier signal source 934 for amplitude control and/or the low frequency modulation signal source 936 to adjust the frequency of the modulation signals to maintain a constant phase of oscillation in the cantilever 926. The phase adjustment control forms a phase lock loop (PLL), yielding cantilever resonance frequency data, while the amplitude control produces mechanical damping of the cantilever in a particular environment. The adjustment in response to environmental changes (such as density or temperature changes in the gaseous or liquid environment) thus can be used to produce a measurement of a characteristic of the environment. In both resonant and steady-state environment, the control signal can produce a measurement of a property of the cantilever itself, such as its stiffness or resonant frequency and damping (otherwise known as "internal friction"). Instrument 920 can also be used to study a cantilever coated, or absorbed with unknown material(s) and response of that cantilever to the environment change such as gaseous, fluidic or temperature environment.

C. Alternative Configurations

As should be apparent from the above, the invention is not limited to systems in which a drive circuit including both a high frequency carrier signal source and a low frequency modulation signal source excites a micro wire to drive a coated cantilever to resonate. Different types of electromagnetic actuators, conductive cantilevers, and/or drive circuits could be used to induce the same or different types of cantilever motion to obtain the same or different measurements than those discussed above. Some possible alternatives will now be discussed, it being understood that these alternatives are provided by way of example and not limitation.

1. Quasistatic Deflection Detection

Figure 21:
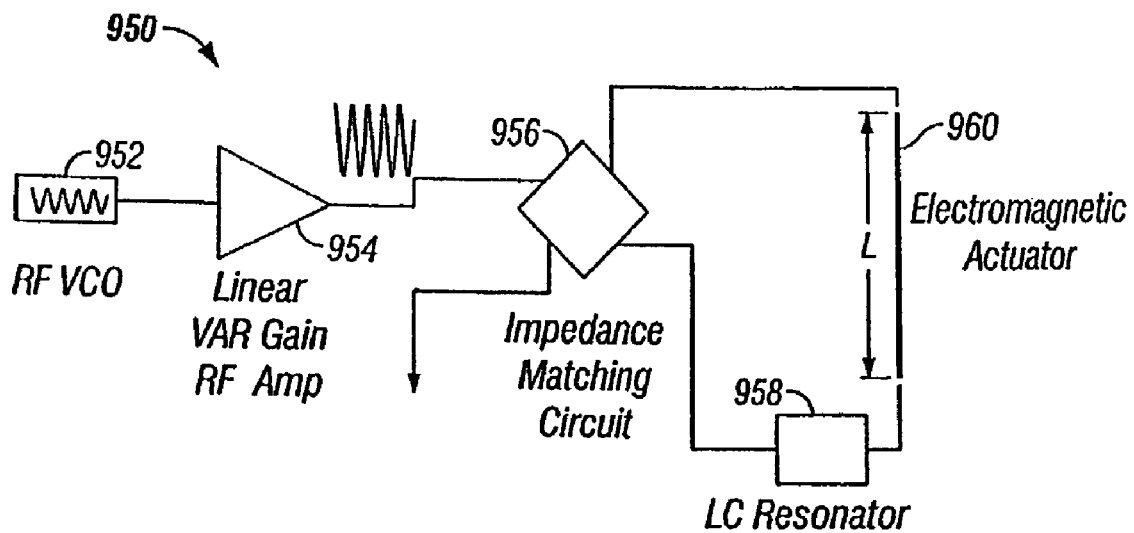
FIG. 21 is a circuit schematic illustrating an alternative electromagnetic drive circuit constructed in accordance with the invention.

All embodiments of the electromagnetic actuator described to this point have combined a high frequency carrier signal source and a low frequency modulation source to drive the cantilever to oscillate, preferably at its resonant frequency or an overtone of half overtone thereof. However, it may be desirable in some instances to induce quasistatic deflection in the cantilever without driving it to oscillate. Quasistatic cantilever deflection can be monitored, e.g., to perform elasticity measurements on a sample which interact with a cantilever probe or to obtain information regarding cantilever stiffness. In this case, a simplified signal source or drive circuit can be employed that lacks a low frequency modulation source. Such a circuit 950 is illustrated schematically in FIG. 21. Circuit 950 differs from the corresponding circuit 808 of FIG. 16 in that the modulation signal source and mixer are omitted. The circuit 980 therefore includes only a high frequency carrier source 952 such as an RF VCO, a linear variable gain amplifier 954, an impedance matching circuit 956, and an LC resonator 958, all of which are configured and operated as described above in connection with FIG. 16. The force imposed on the cantilever when the drive circuit 950 energizes an electromagnetic actuator 960 is essentially steady state (with the RF signal typically having a frequency in the range of 100–200 MHz range). It therefore results in essentially static deflection in the cantilever. In this case, the variable gain amplifier 954 can be used to steadily increase the force imposed on the cantilever, and the cantilever's response to this increase can be monitored.

2. Alternative Electromagnetic Actuator Designs

Figure 22:
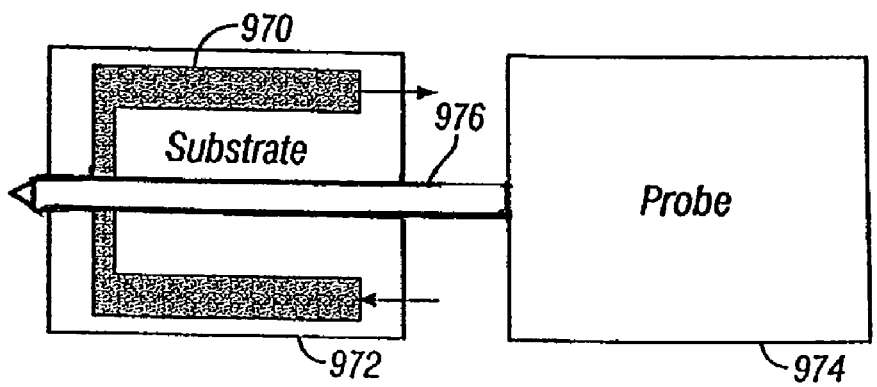
FIG. 22 schematically illustrates an alternative electromagnetic actuator useable in the electromagnetic drive of FIG. 15.

As indicated above, the micro wire forming the electromagnetic actuator of FIG. 15 can be replaced with any other suitably electrically conductive component. One example is a conductive pattern. Hence, referring to FIG. 22, a pattern 970 of a conductive material such as aluminum or gold may be coated or plated on a fixed, non-conductive substrate 972 such as a silicon wafer. The substrate is then positioned such that the pattern faces but is spaced from an electrically conductive surface of the cantilever 976. In the illustrated example, substrate 972 is mounted over the upper conductive surface of the cantilever 976 such that a pattern-bearing surface of the substrate 972 faces downwardly toward the upper surface of cantilever 976. The portion of pattern 970 that crosses the cantilever 976 preferably is located in the same location as the micro wire of the previous embodiments. The pattern 970 can then be energized using, e.g., the drive circuit of FIG. 16 to oscillate the cantilever or the drive circuit of FIG. 21 to quasi-statically deflect the cantilever 976.

3. Alternative Cantilever Designs

Figure 23:
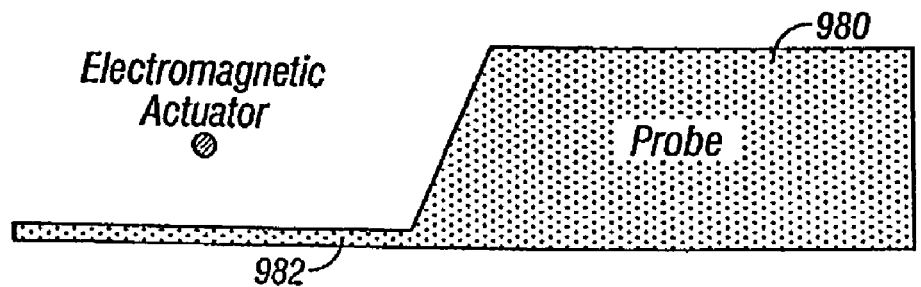
FIG. 23 schematically illustrates an alternative cantilever usable with the electromagnetic drive of FIG. 15.

A cantilever usable in an electromagnetically actuated system could also be rendered electrically conductive by techniques other than by coating a surface of the cantilever with an electrically conductive substance. For instance, the weak conductance of doped silicon, which is widely used in fabricating micro cantilevers, is sufficient for the induced electromagnetic interaction. Probes of this type are most practical in applications not requiring a probe tip. A probe 980 of this type, including its attendant tipless cantilever 982, is schematically illustrated in FIG. 23. Cantilevers that have discontinuous and partial conductive coating are also sufficient to respond to the electromagnetic drive to deform either statically (DC) or dynamically (AC). Non-conductive cantilevers could also conceivably be used in applications in which thermal stress induced forces are of a sufficient magnitude to produce the desired response.

Alternative cantilever configurations are also possible. For instance, a cantilever could have two opposed fixed ends and an unsupported central portion. Another cantilever to which the invention is applicable comprises a fixed membrane with a fixed circumference. In these cases, the electromagnetic actuator and the cantilever are configured to interact with one another to impose a force on a central portion of the cantilever.

Although the best mode contemplated by the inventors for carrying out the present invention is disclosed above, practice of the present invention is not limited thereto. It will be manifest that various additions, modifications and rearrangements of the features of the present invention may be made without deviating from the spirit and scope of the underlying inventive concept. The scope of still other changes to the described embodiments that fall within the present invention but that are not specifically discussed above will become apparent from the appended claims.

We claim:

1. A measurement instrument comprising:
   (A) a probe including a cantilever;
   (B) an electromagnetic actuator spaced from the cantilever; and
   (C) a signal source that is configured to transmit an AC signal to the electromagnetic actuator at a frequency that is substantially higher than the mechanical resonant frequency of the cantilever, the electromagnetic actuator being responsive to the AC signal to impose a force on the cantilever, wherein the AC signal has a frequency of over about 10 MHz.

2. The instrument as recited in claim 1, wherein the electromagnetic actuator comprises a conductive pattern fixed to a non-conductive substrate.

3. The instrument as recited in claim 2, wherein the conductive pattern is fixed on a surface of the substrate that faces and is spaced from the cantilever.

4. The instrument as recited in claim 1, wherein the cantilever and the electromagnetic actuator are configured to be immersed in a gaseous or liquid medium during instrument operation.

5. The instrument as recited in claim 1, wherein the electromagnetic actuator and the cantilever are configured to interact with one another so that the thermal stress caused by the electromagnetic actuator causes the cantilever to deform and oscillate at or below the resonant frequency thereof.

6. The instrument as recited in claim 1, wherein the electromagnetic actuator and the cantilever are configured to interact with one another so that the electrostrictive stress or thermal stresses caused by the electromagnetic actuator causes the cantilever to deform and oscillate at or below the resonant frequency thereof.

7. The instrument as recited in claim 1, wherein at least a portion of the cantilever is magnetic.

8. The instrument as recited in claim 7, wherein the cantilever has a layer of a conductive material coated on at least a portion of at least one surface thereof.

9. The instrument as recited in claim 7, wherein the cantilever is formed from doped silicon.

10. The instrument as recited in claim 1, wherein the electromagnetic actuator comprises a micro wire.

11. The instrument as recited in claim 10, wherein the micro wire has a diameter of less than about 200 microns.

12. The instrument as recited in claim 11, wherein the micro wire has a diameter less than about 50 microns.

13. The instrument as recited in claim 12, wherein the micro wire has a diameter between about 10 microns and about 25 microns.

14. The instrument as recited in claim 10, wherein the micro wire is separated from the cantilever by a gap having a thickness of less than about 200 microns.

15. The instrument as recited in claim 14, wherein the gap has a thickness of about 50 microns.

16. The instrument as recited in claim 1, wherein the AC signal is a radio frequency signal, and wherein the signal source includes a radio frequency carrier signal source that outputs a radio frequency carrier signal.

17. The instrument as recited in claim 16, wherein the AC signal is an unmodulated signal formed from the carrier signal, and wherein the electromagnetic actuator is responsive to the AC signal to impose a quasistatic force on the cantilever.

18. The instrument as recited in claim 1, wherein the AC signal has a frequency between about 100 MHz and about 300 MHz.

19. The instrument as recited in claim 1, wherein the cantilever has a free end portion and has a base supported on a holder, and wherein the electromagnetic actuator and the cantilever are configured to interact with one another to impose a force on the free end portion of the cantilever.

20. A measurement instrument comprising:
(A) a probe including a cantilever;
(B) an electromagnetic actuator spaced from the cantilever; and
(C) a signal source that is configured to transmit an AC signal to the electromagnetic actuator at a frequency that is substantially higher than the mechanical resonant frequency of the cantilever, the electromagnetic actuator being responsive to the AC signal to impose a force on the cantilever, wherein
wherein the AC signal is a radio frequency signal, and wherein the signal source includes a radio frequency carrier signal source that outputs an a radio frequency carrier signal, and wherein
the AC signal is a modulated signal formed by modulating the radio frequency carrier signal with a modulation signal having a frequency that is substantially lower than the frequency of the carrier signal, and wherein the electromagnetic actuator is responsive to the AC signal to drive the cantilever to oscillate.

21. The instrument as recited in claim 20, wherein the modulation signal has a frequency of between about 100 Hz and about 5 MHz.

22. The instrument as recited in claim 20, wherein the instrument is configured to monitor a characteristic of cantilever oscillation while the cantilever interacts with a sample and to obtain an indication of a characteristic of the sample based on the monitoring step.

23. The instrument as recited in claim 22, wherein the modulation signal has a frequency between DC and a quasistatic signal to the fifth overtone of the cantilever resonant frequency.

24. The instrument as recited in claim 22, wherein the instrument further comprises
a detector that monitors cantilever oscillation,
a computer that is operatively coupled to the detector, that compares a monitored parameter of cantilever oscillation to a setpoint, and that generates an error signal as a result of the comparison, and
a translational actuator that is operatively coupled to the computer and that moves one of the probe and the sample relative to the other of the probe and the sample so as to make the monitored cantilever oscillation parameter at least approach the setpoint.

25. The instrument as recited in claim 24, further comprising a feedback circuit that determines gains for the error signal and the drive voltage required to move the translational actuators to maintain the setpoint.

26. The instrument as recited in claim 24, wherein the monitored cantilever oscillation parameter is cantilever oscillation amplitude, and wherein the translational actuator comprises a Z actuator that moves at least one of the probe and the sample vertically relative to the other of the probe and the sample in response to the receipt of the error signal.

27. The instrument as recited in claim 20, further comprising:
a detector that monitors cantilever oscillation, and
a computer that
is operatively coupled to the detector,
compares a monitored parameter of cantilever oscillation to a setpoint,
generates an error signal as a result of the comparison, and
transmits the error signal to the one of a feedback gain control operator and a phase lock loop so as to make the monitored oscillation parameter at least approach the setpoint.

28. The instrument as recited in claim 27, wherein the setpoint parameter is one of an oscillation amplitude setpoint and an oscillation phase setpoint.

29. The instrument as recited in claim 27, wherein the instrument is configured to operate in the absence of a sample external to the cantilever to obtain information regarding a characteristic of at least one of the probe and the environment.

30. The instrument as recited in claim 20, wherein the signal source further comprises a low frequency modulation signal source that is configured to supply the modulation signal, and a mixer that is configured to
(1) receive the carrier signal and the modulation signal from the carrier signal source and the modulation signal source, respectively,
(2) produce the AC signal from the carrier signal and the modulation signal, and
(3) transmit the AC signal to the electromagnetic actuator.

31. The instrument as recited in claim 20, wherein the signal source further comprises
a variable gain amplifier that is configured to amplify the AC signal after the AC signal is output from the mixer,
an impedance matching circuit that is configured to match the impedance of the AC signal to the impedance of the electromagnetic actuator, and an LC resonator that is configured to enhance a drive efficiency of the electromagnetic actuator.

32. A method comprising:
(A) transmitting an AC signal to an electromagnetic actuator of an instrument, the AC signal having a frequency that is substantially higher than a resonant frequency of a cantilever of a probe of the instrument,
(B) in response to the transmission of the AC signal to the electromagnetic actuator, imposing a force on the cantilever, wherein the AC signal has a frequency of over about 10 MHz.

33. A method comprising:
(A) transmitting an AC signal to an electromagnetic actuator of an instrument, the AC signal having a frequency that is substantially higher than a resonant frequency of a cantilever of a probe of the instrument,
(B) in response to the transmission of the AC signal to the electromagnetic actuator, imposing a force on the cantilever, wherein
the AC signal is a radio frequency signal formed by modulating a radio frequency carrier signal with a relatively low frequency modulation signal, and wherein the electromagnetic actuator drives the cantilever to oscillate in response to the transmission of the AC signal thereto.

34. The method as recited in claim 33, wherein the carrier signal has a frequency between about 100 MHz and 300 MHz.

35. The method as recited in claim 33, wherein the modulation signal has a frequency of between about 100 Hz and about 5 MHz.

36. The method as recited in claim 33, further comprising monitoring a characteristic of cantilever oscillation while the cantilever interacts with a sample and obtaining an indication of a characteristic of the sample based on the monitoring step.

37. The method as recited in claim 33, further comprising monitoring a characteristic of cantilever oscillation in the absence of an external sample and obtaining an indication of a characteristic of at least one of the cantilever or cantilever arrays and the environment based on the monitoring step.

38. The method as recited in claim 33, wherein the AC signal is a radio frequency signal formed from a radio frequency carrier signal without modulating the carrier signal with a relatively low frequency modulation signal, and wherein the imposing step imposes a quasistatic force on the cantilever.

39. The method as recited in claim 38, further comprising obtaining elasticicity measurements of a sample while imposing the quasistatic force on the cantilever.

40. An instrument comprising:
  (A) a probe including an electrically conductive cantilever;
  (B) actuator means for imposing a force on the cantilever; and
  (C) means for transmitting an AC signal to the actuator means to energize the actuator means, the AC signal having a frequency that is substantially higher than a resonant frequency of the cantilever, wherein
  the AC signal is a radio frequency signal, and further comprising means for forming the AC signal by modulating a radio frequency carrier signal with a relatively low frequency modulation signal, and wherein the actuator means is responsive to the means for transmitting to drive the cantilever to oscillate.

41. The instrument as recited in claim 40, wherein the means for forming comprises a signal source that includes a radio frequency carrier signal source that is configured to supply the carrier signal, a low frequency modulation signal source that is configured to supply the modulation signal, and a mixer that is configured to
  (1) receive the carrier signal and the modulation signal from the carrier signal source and the modulation signal source, respectively,
  (2) produce the modulated carrier signal from the carrier signal and the modulation signal, and
  (3) transmit the modulated carrier signal to the actuator means to drive the cantilever to oscillate.

* * * * *